(12) United States Patent
Mathiesen et al.

(10) Patent No.: US 12,083,164 B2
(45) Date of Patent: *Sep. 10, 2024

(54) AMYLIN ANALOGUES

(71) Applicant: Zealand Pharma A/S, Søborg (DK)

(72) Inventors: Jesper Mosolff Mathiesen, Farum (DK); Jesper Skodborg Villadsen, Skovlunde (DK); Lise Giehm, Frederiksberg (DK); Henrik Kofoed Munch, Frederiksberg (DK); Dieter Wolfgang Hamprecht, Pozzolengo (IT); Alexander Heim-Riether, Ingelheim am Rhein (DE); Giacomo Fossati, Ingelheim am Rhein (DE)

(73) Assignee: Zealand Pharma A/S, Søborg (DK)

( * ) Notice: Subject to any disclaimer, the term of this patent is extended or adjusted under 35 U.S.C. 154(b) by 112 days.

This patent is subject to a terminal disclaimer.

(21) Appl. No.: 17/381,373

(22) Filed: Jul. 21, 2021

(65) Prior Publication Data

US 2021/0346468 A1 Nov. 11, 2021

Related U.S. Application Data

(63) Continuation of application No. 16/664,168, filed on Oct. 25, 2019, now Pat. No. 11,382,956, which is a continuation of application No. 16/050,102, filed on Jul. 31, 2018, now abandoned, which is a continuation of application No. 15/698,743, filed on Sep. 8, 2017, now Pat. No. 10,071,140.

(30) Foreign Application Priority Data

Sep. 9, 2016 (EP) .................... 16188024

(51) Int. Cl.
*A61K 38/00* (2006.01)
*A61K 38/22* (2006.01)
*C07K 14/575* (2006.01)

(52) U.S. Cl.
CPC ............ *A61K 38/22* (2013.01); *C07K 14/575* (2013.01)

(58) Field of Classification Search
CPC .............................. A61K 38/22; C07K 14/575
See application file for complete search history.

(56) References Cited

U.S. PATENT DOCUMENTS

| | | | |
|---|---|---|---|
| 5,424,394 A | 6/1995 | Lehman de Gaeta et al. | |
| 5,686,411 A | 11/1997 | Gaeta et al. | |
| 5,998,367 A | 12/1999 | Gaeta et al. | |
| 7,407,934 B2 | 8/2008 | Kolterman et al. | |
| 7,910,548 B2 | 3/2011 | Duft et al. | |
| 8,575,090 B2 | 11/2013 | Schaeffer et al. | |
| 8,575,091 B1 | 11/2013 | Dahl et al. | |
| 8,722,849 B2 | 5/2014 | Schaeffer et al. | |
| 8,741,836 B2 | 6/2014 | Schaeffer et al. | |
| 8,895,504 B2 | 11/2014 | Schaffer et al. | |
| 9,023,789 B2 | 5/2015 | Dahl et al. | |
| 10,071,140 B2 | 9/2018 | Mathiesen et al. | |
| 10,766,939 B2 | 9/2020 | Just et al. | |
| 11,382,956 B2 | 7/2022 | Mathiesen et al. | |
| 2002/0187923 A1 | 12/2002 | Gaeta et al. | |
| 2008/0274952 A1 | 11/2008 | Soares et al. | |
| 2010/0221240 A1 | 9/2010 | Kapurniotu et al. | |
| 2013/0005646 A1 | 1/2013 | Schaeffer et al. | |
| 2013/0059770 A1 | 3/2013 | Schaeffer et al. | |
| 2014/0018286 A1 | 1/2014 | Schaeffer et al. | |
| 2014/0087995 A1 | 3/2014 | Dahl et al. | |
| 2016/0184401 A1 | 6/2016 | Trambaioli Da Rocha E Lima et al. | |
| 2016/0272693 A1 | 9/2016 | Just et al. | |
| 2018/0071366 A1 | 3/2018 | Mathiesen et al. | |

FOREIGN PATENT DOCUMENTS

| | | |
|---|---|---|
| CL | 47901 B1 | 9/2005 |
| CL | 2017002256 A1 | 4/2018 |
| KR | 10-2017-0126504 A | 11/2017 |
| WO | WO-91/07978 A1 | 6/1991 |
| WO | WO-92/11862 A1 | 7/1992 |
| WO | WO-93/10146 A1 | 5/1993 |
| WO | WO-98/08871 A1 | 3/1998 |
| WO | WO-98/11125 A1 | 3/1998 |
| WO | WO-98/26796 A1 | 6/1998 |
| WO | WO-98/50059 A1 | 11/1998 |
| WO | WO-98/55144 A1 | 12/1998 |
| WO | WO-99/34764 A2 | 7/1999 |
| WO | WO-00/55119 A1 | 9/2000 |
| WO | WO-2000/055184 A1 | 9/2000 |
| WO | WO-2005/000222 A2 | 1/2005 |
| WO | WO-2005/077072 A2 | 8/2005 |
| WO | WO-2006/042745 A2 | 4/2006 |
| WO | WO-2006/083254 A1 | 8/2006 |

(Continued)

OTHER PUBLICATIONS

Baisley et al., "Amylin receptor signaling in the nucleus accumbens negatively modulates μ-opioid-driven feeding," Neuropsychopharmacology 39(13):3009-17 (2014) (9 pages).

Bogdanowich-Knipp et al., "Solution stability of linear vs. cyclic RGD peptides," J Pept Res. 53(5):530-41 (1999).

Chai et al., "Characterization of binding sites for amylin, calcitonin, and CGRP in primate kidney," Am J Physiol. 274(1 Pt 2):F51-62 (1998).

(Continued)

*Primary Examiner* — Jeanette M Lieb
(74) *Attorney, Agent, or Firm* — Clark & Elbing LLP

(57) ABSTRACT

The present invention relates to amylin analogues and to their use in the treatment or prevention of a variety of diseases, conditions or disorders, including obesity, excess food intake and associated metabolic diseases such as diabetes. The analogues have good physical and chemical stability, good solubility, and a long duration of action, and are well suited for use in the form of a liquid formulation.

30 Claims, No Drawings
Specification includes a Sequence Listing.

(56) References Cited

FOREIGN PATENT DOCUMENTS

| WO | WO-2007/022123 A2 | 2/2007 |
| --- | --- | --- |
| WO | WO-2007/104789 A2 | 9/2007 |
| WO | WO-2008/101017 A2 | 8/2008 |
| WO | WO-2008/152403 A1 | 12/2008 |
| WO | WO-2009/034118 A1 | 3/2009 |
| WO | WO-2009/034119 A1 | 3/2009 |
| WO | WO-2010/046357 A1 | 4/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/107874 A2 | 9/2010 |
| WO | WO-2011/006497 A1 | 1/2011 |
| WO | WO-2011/064282 A1 | 6/2011 |
| WO | WO-2011/160630 A2 | 12/2011 |
| WO | WO-2011/160633 A1 | 12/2011 |
| WO | WO-2012/168430 A2 | 12/2012 |
| WO | WO-2012/168431 A2 | 12/2012 |
| WO | WO-2012/168432 A1 | 12/2012 |
| WO | WO-2013/092703 A2 | 6/2013 |
| WO | WO-2013/156594 A1 | 10/2013 |
| WO | WO-2014/041195 A1 | 3/2014 |
| WO | WO-2014/197961 A1 | 12/2014 |
| WO | WO-2015/040182 A2 | 3/2015 |
| WO | WO-2015/050182 A1 | 4/2015 |
| WO | WO-2015/055801 A1 | 4/2015 |
| WO | WO-2015/055802 A2 | 4/2015 |
| WO | WO-2015/150564 A1 | 10/2015 |
| WO | WO-2015/168488 A2 | 11/2015 |
| WO | WO-2016/034604 A1 | 3/2016 |
| WO | WO-2016/100456 A2 | 6/2016 |
| WO | WO-2016/146739 A1 | 9/2016 |
| WO | WO-2018/144671 A1 | 8/2018 |

OTHER PUBLICATIONS

Database Geneseq [Online] Jun. 14, 2007, "Hybrid polypeptide amylin analog parent molecule Seq Id No. 78.", XP002739549, retrieved from EBI accession No. GSP:AFC32081 Database accession No. AFC32081 (1 page).

Fortin et al., "Wildlife sequences of islet amyloid polypeptide (IAPP) identify critical species variants for fibrillization," Amyloid. 22(3):194-202 (2015) (9 pages). doi: 10.3109/13506129.2015. 1070824.

He et al., "Synthesis and chemical stability of a disulfide bond in a model cyclic pentapeptide: Cyclo(1,4)-Cys-Gly-Phe-Cys-Gly-OH," J Pharm Sci. 95(10):2222-34 (2006).

International Preliminary Report on Patentability for International Application No. PCT/EP2016/055793, dated Jun. 9, 2017 (37 pages).

International Search Report and Written Opinion for International Application No. PCT/EP2016/055793, dated Jun. 24, 2016 (16 pages).

International Search Report and Written Opinion for International Application No. PCT/EP2017/072718, dated Jan. 3, 2018 (13 pages).

Kajava et al., "A model for Ure2p prion filaments and other amyloids: the parallel superpleated beta-structure," Proc Natl Acad Sci U.S.A. 101(21):7885-90 (2004) (8 pages).

Koo et al., "Amide inequivalence in the fibrillar assembly of islet amyloid polypeptide," Protein Eng Des Sel. 21(3):147-54 (2008).

Li et al., "Suppression of polyglutamine toxicity by the yeast Sup35 prion domain in *Drosophila*," J Biol Chem. 282(52):37694-701 (2007) (9 pages).

Moriarty et al., "Effects of sequential proline substitutions on amyloid formation by human amylin20-29," Biochemistry 38(6):1811-8 (1999).

Muthusamy et al., "Design and study of peptide-based inhibitors of amylin cytotoxicity," Bioorg Med Chem Lett. 20(4):1360-2 (2010).

Reidelberger et al., "Effects of amylin-related peptides on food intake, meal patterns, and gastric emptying in rats," Am J Physiol Regul Integr Comp Physiol. 282(5):R1395-404 (2002).

Rijkers et al., "Inhibition of amyloid fibril formation of human amylin by N-alkylated amino acid and alpha-hydroxy acid residue containing peptides," Chemistry 8(18):4285-91 (2002).

Tenidis et al., "Identification of a penta- and hexapeptide of islet amyloid polypeptide (IAPP) with amyloidogenic and cytotoxic properties," J Mol Biol. 295(4):1055-71 (2000).

Trivedi et al., "The role of thiols and disulfides on protein stability," Curr Protein Pept Sci. 10(6):614-25 (2009).

Tsai et al., "Energy landscape of amyloidogenic peptide oligomerization by parallel-tempering molecular dynamics simulation: significant role of Asn ladder," Proc Natl Acad Sci U.S.A. 102(23):8174-9 (2005) (9 pages).

Westermark et al., "Islet amyloid polypeptide: pinpointing amino acid residues linked to amyloid fibril formation," Proc Natl Acad Sci U.S.A. 87(13):5036-40 (1990).

Wineman-Fisher et al., "The removal of disulfide bonds in amylin oligomers leads to the conformational change of the 'native' amylin oligomers," Phys Chem Chem Phys. 18(18):12438-42 (2016).

Yan et al., "Design of a mimic of nonamyloidogenic and bioactive human islet amyloid polypeptide (IAPP) as nanomolar affinity inhibitor of IAPP cytotoxic fibrillogenesis," Proc Natl Acad Sci U.S.A. 103(7):2046-51 (2006).

Yan et al., "Selectively N-methylated soluble IAPP mimics as potent IAPP receptor agonists and nanomolar inhibitors of cytotoxic self-assembly of both IAPP and Abeta40," Angew Chem Int Ed Engl. 52(39):10378-83 (2013).

Groenning et al., "Study on the binding of Thioflavin T to beta-sheet-rich and non-beta-sheet cavities," J Struct Biol. 158:358-69 (2007).

Groenning, Minna, "Binding mode of Thioflavin T and other molecular probes in the context of amyloid fibrils—current status," J Chem Biol. 3(1):1-18 (2010).

Haffner et al., "Intensive lifestyle intervention or metformin on inflammation and coagulation in participants with impaired glucose tolerance," Diabetes. 54(5):1566-72 (2005).

Knudsen et al., "Potent derivatives of glucagon-like peptide-1 with pharmacokinetic properties suitable for once daily administration," J Med Chem. 43(9):1664-9 (2000).

Madsen et al., "Structure-activity and protraction relationship of long-acting glucagon-like peptide-1 derivatives: importance of fatty acid length, polarity, and bulkiness," J Med Chem. 50(24):6126-32 (2007).

LeVine, "Thioflavine T interaction with synthetic Alzheimer's disease beta-amyloid peptides: Detection of amyloid aggregation in solution," Protein Science. 2(3): 404-410 (1993).

Redalieu et al., "Pharmacokinetic Effects of Syringe Mixing Pramlintide, Isophane Insulin, and Soluble Insulin," Diabetology. 1399:A 356 (1997) (1 page).

AMYLIN ANALOGUES

PRIORITY

This application claims priority from European patent application no. 16188024.0, filed 9 Sep. 2016, disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 20, 2021, is named "50412-105004_Sequence_Listing_07_20_21_ST25" and is 98,794 bytes in size.

FIELD OF THE INVENTION

The present invention relates to amylin analogues that are amylin receptor agonists, and to their medical use in the treatment and/or prevention of a variety of diseases, conditions or disorders, including treatment and/or prevention of excess food intake, obesity and excess body weight, metabolic diseases, and other conditions and disorders described herein. In particular, the present invention relates to stable amylin analogues that have a long duration of action and are well suited for use in the form of a liquid formulation.

BACKGROUND OF THE INVENTION

Amylin is one of a family of peptide hormones that includes amylin, calcitonin, calcitonin gene-related peptide, adrenomedullin and intermedin (intermedin also being known as AFP-6), and has been implicated in various metabolic diseases and disorders. Human amylin was first isolated, purified and characterized as the major component of amyloid deposits in the islets of pancreases from type 2 diabetes patients.

Native human amylin is a 37-amino acid peptide having the formula

H-KC( )NTATC( )ATQRLANFLVHSSNNF-
GAILSSTNVGSNTY-NH$_2$ wherein H- at the N-terminus designates a hydrogen atom, corresponding to the presence of a free amino group on the N-terminal amino acid residue [i.e. the lysine (K) residue at sequence position number 1 in the sequence shown above]; wherein —NH$_2$ at the C-terminus indicates that the C-terminal carboxyl group is in the amide form; and wherein the parentheses ( ) associated with the two cysteine (C, Cys) residues at sequence positions 2 and 7 indicate the presence of an intramolecular disulfide bridge between the two Cys residues in question.

Amylin may be beneficial in treating metabolic disorders such as diabetes and/or obesity. Amylin is believed to regulate gastric emptying, and to suppress glucagon secretion and food intake, thereby regulating the rate of glucose release to the circulation. Amylin appears to complement the actions of insulin. Compared to healthy adults, type 1 diabetes patients have no circulating amylin, and type 2 diabetes patients exhibit reduced postprandial amylin concentrations. In human trials an amylin analogue known as pramlintide, described in WO 93/10146 and having the sequence Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr, which also possesses a disulphide bridge between the Cys residues at positions 2 and 7, has been shown to reduce body weight or reduce weight gain. An alternative amylin analogue incorporating N-methylated residues and having a reduced tendency to fibrillation, designated IAPP-GI, has been described by Yan et al. (PNAS, 103(7), 2046-2051, 2006; Angew. Chem. Int. Ed. 2013, 52, 10378-10383; WO2006/042745). IAPP-GI appears to have lower activity than native amylin, however.

WO91/07978 describes analogues of hypocalcemic peptides, including amylin, in which internal disulphide bridges are replaced with alternative cyclisations. The effect of these alternative structures on the activity of amylin analogues is not disclosed. WO99/34764 presents data showing that $^{2,7}$cyclo-[2Asp,7Lys]-h-amylin has considerably lower potency than certain other amylin analogues, and human amylin itself.

Further analogues of amylin or pramlintide are described in WO2013/156594, WO2012/168430, WO2012/168431 and WO2012/168432, as well as WO2015/040182.

Obesity is believed to be a major causal factor in development of type 2 diabetes, which constitutes a growing and worldwide major health problem. Diseases or disorders that may develop as a consequence of untreated diabetes include cardiovascular and peripheral artery disease, micro- and macrovascular complications, stroke, and certain forms of cancer, particularly hematopoietic cancers.

There is a need in the art for further amylin analogues. For example, amylin analogues that show a reduced tendency for fibrillation and/or high chemical stability at or around pH 7 might allow for a formulation at or near physiological pH. Amylin analogues having appropriately long plasma elimination half-lives, may also enable longer intervals between dosing than is currently possible (e.g. once weekly, or even less frequently) and hence improve patient compliance. High levels of agonist activity at the amylin receptor may also be desirable.

SUMMARY OF THE INVENTION

The present invention relates to compounds which are analogues of human amylin.

In a first aspect, the invention provides an amylin analogue which is a compound having the formula:

R$^1$—Z—R$^2$ wherein

R$^1$ is hydrogen, C$_{1-4}$ acyl, benzoyl or C$_{1-4}$ alkyl, or a half-life extending moiety M, wherein M is optionally linked to Z via a linker moiety L;

R$^2$ is OH or NHR$^3$, wherein R$^3$ is hydrogen or C$_{1-3}$-alkyl; and

Z is an amino acid sequence of formula I:

(I)
(SEQ ID NO: 3)
X1-X2-X3-X4-X5-X6-X7-Ala-Thr-X10-Arg-Leu-Ala-

X14-Phe-Leu-X17-Arg-X19-X20-Phe-Gly(Me)-Ala-

Ile(Me)-X27-Ser-Ser-Thr-Glu-X32-Gly-Ser-X35-

Thr-X37 wherein

X1 is selected from the group consisting of Arg, Lys and Glu;

X3 is selected from the group consisting of Gly, Gln and Pro;

X4 is selected from the group consisting of Thr and Glu;

X5 is selected from the group consisting of Ala and Leu;

X6 is selected from the group consisting of Thr and Ser;

X10 is selected from the group consisting of Glu and Gln;

X14 is selected from the group consisting of Aad, His, Asp, Asn and Arg;

X17 is selected from the group consisting of Gln, His and Thr;

X19-X20 is selected from Ser-Ser, Thr-Thr, Ala-Thr, Ala-Ala, Gly-Thr, Gly-Gly and Ala-Asn or is absent;

X27 is selected from the group consisting of Leu and Pro;

X32 is selected from the group consisting of Val and Thr;

X35 is selected from the group consisting of Asn and Ser;

X37 is selected from the group consisting of Hyp and Pro; and

X2 and X7 are amino acid residues whose side chains together form a lactam bridge; or a pharmaceutically acceptable salt or solvate thereof.

In some embodiments, X1 is selected from Arg and Lys.

In some embodiments, X3 is Gly, X4 is Thr, X5 is Ala and/or X6 is Thr, e.g. X3 is Gly, X4 is Thr, X5 is Ala and X6 is Thr.

In some embodiments, X14 is selected from His, Asp and Aad.

In some embodiments, X17 is Gln.

In some embodiments, X19-X20 is selected from Ser-Ser and Thr-Thr, or is absent, e.g. Ser-Ser.

In some embodiments, X32 is Val, X35 is Asn and/or X37 is Hyp.

Thus, Z may be an amino acid sequence of formula II:

(II)
(SEQ ID NO: 4)
X1-X2-Gly-Thr-Ala-Thr-X7-Ala-Thr-X10-Arg-

Leu-Ala-X14-Phe-Leu-Gln-Arg-X19-X20-Phe-

Gly(Me)-Ala-Ile(Me)-X27-Ser-Ser-Thr-Glu-

Val-Gly-Ser-Asn-Thr-Hyp wherein

X1 is selected from the group consisting of Arg and Lys;

X10 is selected from the group consisting of Glu and Gln;

X14 is selected from the group consisting of Aad, Asp and His;

X19-X20 is selected from Ser-Ser and Thr-Thr or is absent;

X27 is selected from the group consisting of Leu and Pro; and

X2 and X7 are amino acid residues whose side chains together form a lactam bridge.

In some embodiments, X14 is Aad, X19-X20 is Ser-Ser and X27 is Leu.

Throughout this specification, amino acid positions of the amylin analogues are numbered according to the corresponding position in native human amylin having the sequence shown above. The sequence of Formulae I and II (and other formulae herein) contain a two amino acid deletion corresponding to the two residues Asn21 and Asn22 of human amylin. Thus, for ease of comparison with the amylin sequence, the Phe residue immediately C-terminal (downstream) of position X20 is designated as position 23, since it aligns with Phe23 of human amylin. Thus, the numbering of any given residue in Formulae I and II above, and in other formulae elsewhere in this specification, reflects the corresponding residue in human amylin when optimally aligned therewith and does not necessarily reflect its linear position in the particular sequence.

(It will be apparent that any of the relevant formulae presented in this specification could be written to include residues X21-X22 at the appropriate positions, wherein X21 and X22 are absent.)

Native amylin is known to form fibrils in aqueous solution almost instantly. Consequently, many attempts have been made to enhance the stability of amylin analogues in liquid formulations. The tendency for fibrillation can be reduced by incorporating N-methylated residues (as mentioned above) and/or by substitution of certain amino acids at various positions. However, despite these options the desire to further optimize the stability of amylin analogues in aqueous solution remains. Amylin analogues with further enhanced chemical stability in aqueous solution would facilitate development of a corresponding pharmaceutical product, potentially even in the form of a ready-to-use formulation, e.g. at or around the neutral pH range (pH 7-7.4).

Native amylin, and the vast majority of amylin analogues (such as pramlintide) contain a disulphide bridge between cysteine residues at positions 2 and 7. The internal cyclisation which this bridge provides appears to be required for full potency and activity. Although compounds containing an internal disulphide bond are frequently less chemically stable than might be desired, and the presence of the bond may contribute to dimerisation and oligomerisation, e.g. via disulphide exchange reactions, the disulphide bond in amylin or amylin analogues has not been reported to be a factor relevant for the low chemical stability in aqueous formulations.

Few attempts to replace the disulphide bridge in amylin have been reported. As described above, in an attempt to enhance in vivo stability and efficacy by reducing chemical and enzymatic proteolysis, WO91/07978 proposes replacing internal disulphide bridges of hypocalcemic peptides (including e.g. calcitonin and amylin) with alternative cyclisations. However, the effect of these alternative structures on the activity of amylin analogues is not disclosed. WO99/34764 presents data showing that replacement of the disulphide bridge with an intramolecular lactam bridge in the native human amylin sequence results in an amylin analogue ($^{2,7}$cyclo-[2Asp,7Lys]-h-amylin) having considerably lower potency than the wild type and many other amylin analogues, which may further explain why alternative cyclisation options have not been pursued further.

However, it has now been found that lactam-based cyclisations are very compatible with amylin analogues having deletions at positions 21 and 22, as the replacement of the disulphide bridge by a lactam bridge leads to a substantial increase of stability in aqueous solution (see table 2) while other beneficial properties of these amylin analogues, such as low tendency for fibrillation, high activity and good solubility are retained. Although it is known that such lactam bridges reduce the activity of the peptides dramatically (see WO 91/07978, p 45 lines 36 to 52; WO 99/34764 p. 84, Table A), in addition it has now been found that amylin analogues of the present invention may retain high activity/ show no reduction of activity at the hCT-R, hAMYR1, hAMYR2 and/or hAMYR3 receptors. Additionally or alternatively they may have excellent chemical stability and resistance to fibrillation, especially but not exclusively in the neutral pH range.

Thus the amylin analogue of the invention comprises a lactam bridge formed between the side chains of the residues at positions X2 and X7. For simplicity, positions 2 and 7 will be discussed by reference to the residues nominally present before lactam formation.

One of the residues at positions X2 and X7 is a residue with a side chain comprising a carboxylic acid group and the other is a residue with a side chain comprising an amine group, wherein a lactam (cyclic amide) is formed between the carboxylic acid and amine groups. The amine may be a primary or secondary amine, but is typically a primary amine. Suitable amino acids whose side chains can participate in a lactam bridge include Asp, Glu and Aad (having side chains comprising carboxylic acid groups) and Dap, Dab, Orn, Lys and hLys (having side chains comprising amine groups). Any of the amino acids selected from Asp, Glu and Aad may in principle form a lactam bridge with any of the amino acids selected from the group consisting of Dap, Dab, Orn, Lys and hLys.

Thus, one of the residues at position X2 and X7 may be selected from Asp, Glu and Aad, and the other may be selected from Dap, Dab, Orn, Lys and hLys.

In some embodiments the carboxylic acid component of the lactam bridge derives from the amino acid at position X2, whereas the amine component of the lactam bridge derives from the amino acid at position X7. Thus X2 may be selected from Asp, Glu and Aad, and X7 may be selected from Dap, Dab, Orn, Lys and hLys.

It may be beneficial that the side chain of the residue at position X2 is of the same length as, or shorter than, the side chain of the residue at position X7. Such residue combinations can provide benefits including higher potency as compared to other combinations.

In this context, side chain length is counted as the number of atoms in a linear chain from the first atom of the side chain (which is bonded to an atom of the peptide backbone, i.e. to the alpha carbon of the relevant residue for most amino acids) up to and including the atom which participates in the amide bond of the lactam bridge (i.e. the carbon atom of the carboxylic acid functional group or the nitrogen atom of the amine group).

Thus common acid- and amine-containing side chains are considered to have the following side chain lengths:
Asp: 2 atoms
Glu: 3 atoms
Aad: 4 atoms
Dap: 2 atoms
Dab: 3 atoms
Orn: 4 atoms
Lys: 5 atoms
hLys: 6 atoms In some embodiments the side chain of the residue at position X2 is shorter than the side chain of the residue at position X7.

Desirably, the length of the lactam bridge provided by the two side chains after formation of the amide bond (not including any atoms in the peptide backbone) is 4, 5, 6, 7 or 8 atoms, e.g. 5, 6, 7 or 8 atoms, or 5, 6 or 7 atoms.

Thus, suitable pairings of residues at positions X2 and X7 in which the side chain at position X2 is shorter than the side chain at position X7 include:
X2 is Asp and X7 is Lys
X2 is Asp and X7 is Orn
X2 is Asp and X7 is Dab
X2 is Asp and X7 is hLys
X2 is Dap and X7 is Aad Examples of suitable pairings having the same side chain lengths include:
X2 is Glu and X7 is Dab
X2 is Dab and X7 is Glu Further pairings which may nevertheless be considered include:
X2 is Asp and X7 is Dap
X2 is Aad and X7 is Dap
X2 is Dap and X7 is Asp
X2 is Dab and X7 is Asp
X2 is Orn and X7 is Asp Pairings of particular interest are:
X2 is Asp and X7 is Lys
X2 is Asp and X7 is Orn.

In some embodiments of the formulae described above:
X1 may be Arg;
X10 may be Glu.
X14 may be selected from Asp and Aad.
X19-X20 may be Ser-Ser
X27 may be Leu
The amylin analogue may have the formula:

$$R^1\text{—}Z\text{—}R^2$$

wherein $R^1$ is hydrogen, $C_{1-4}$ acyl, benzoyl or $C_{1-4}$ alkyl, or a half-life extending moiety M, wherein M is optionally linked to Z via a linker moiety L;

$R^2$ is OH or $NHR^3$, wherein $R^3$ is hydrogen or $C_{1-3}$-alkyl; and

Z is an amino acid sequence selected from the group consisting of:

```
                                           (SEQ ID NO: 5)
RD()GTAT-Dap()-ATERLAHFLQRSSF-Gly(Me)-A-

Ile(Me)-LSSTEVGSNT-Hyp (SEQ ID NO: 6)
RD()GTAT-Dab()-ATERLAHFLQRSSF-Gly(Me)-A-

Ile(Me)-LSSTEVGSNT-Hyp (SEQ ID NO: 7)
RD()GTAT-Orn()-ATERLAHFLQRSSF-Gly(Me)-A-

Ile(Me)-LSSTEVGSNT-Hyp (SEQ ID NO: 8)
RD()GTAT-Orn()-ATERLAHFLQRSSF-Gly(Me)-A-

Ile(Me)-PSSTEVGSNT-Hyp (SEQ ID NO: 9)
RD()GTAT-Orn()-ATERLAHFLQRF-Gly(Me)-A-

Ile(Me)-LSSTEVGSNT-Hyp (SEQ ID NO: 10)
RD()GTAT-Orn()-ATERLAHFLHRSSF-Gly(Me)-A-

Ile(Me)-LSSTEVGSNTP (SEQ ID NO: 11)
RD()GTAT-Orn()-ATQRLAHFLQRSSF-Gly(Me)-A-

Ile(Me)-LSSTEVGSNT-Hyp (SEQ ID NO: 12)
RD()GTAT-Orn()-ATQRLAHFLQRSSF-Gly(Me)-A-

Ile(Me)-PSSTEVGSNT-Hyp
```

(SEQ ID NO: 13)
RD()GTAT-Orn()-ATERLARFLQRSSF-Gly(Me)-A-Ile(Me)-LSSTEVGSNT-Hyp (SEQ ID NO: 14)
ED()GTATK()ATERLAHFLQRSSF-Gly(Me)-A-Ile(Me)-LSSTEVGSNT-Hyp (SEQ ID NO: 15)
RD()GEATK()ATERLAHFLQRSSF-Gly(Me)-A-Ile(Me)-LSSTEVGSNT-Hyp (SEQ ID NO: 16)
RD()GTLTK()ATERLAHFLQRSSF-Gly(Me)-A-Ile(Me)-LSSTEVGSNT-Hyp (SEQ ID NO: 17)
RD()GTASK()ATERLAHFLQRSSF-Gly(Me)-A-Ile(Me)-LSSTEVGSNT-Hyp (SEQ ID NO: 18)
RD()GTATK()ATQRLAHFLQRSSF-Gly(Me)-A-Ile(Me)-PSSTEVGSNT-Hyp (SEQ ID NO: 19)
RD()GTATK()ATQRLAHFLQRSSF-Gly(Me)-A-Ile(Me)-LSSTEVGSNT-Hyp (SEQ ID NO: 20)
RD()GTATK()ATERLAHFLQRSSF-Gly(Me)-A-Ile(Me)-PSSTEVGSNT-Hyp (SEQ ID NO: 21)
RD()GTATK()ATERLAHFLQRSSF-Gly(Me)-A-Ile(Me)-LSSTEVGSNT-Hyp (SEQ ID NO: 22)
RD()GTAT-hLys()-ATERLAHFLQRSSF-Gly(Me)-A-Ile(Me)-LSSTEVGSNT-Hyp (SEQ ID NO: 23)
RD()GTAT-Orn()-ATERLA-Aad-FLQRSSF-Gly(Me)-A-Ile(Me)-LSSTEVGSNT-Hyp (SEQ ID NO: 24)
RD()GTAT-Orn()-ATERLA-Aad-FLQRSSF-Gly(Me)-A-Ile(Me)-PSSTEVGSNT-Hyp (SEQ ID NO: 25)
RD()GTAT-Orn()-ATERLA-Aad-FLTRSSF-Gly(Me)-A-Ile(Me)-LSSTEVGSST-Hyp (SEQ ID NO: 26)
RD()GTAT-Orn()-ATERLA-Aad-FLQRTTF-Gly(Me)-A-Ile(Me)-LSSTEVGSNT-Hyp (SEQ ID NO: 27)
RD()GTAT-Orn()-ATERLA-Aad-FLQRTTF-Gly(Me)-A-Ile(Me)-PSSTEVGSNT-Hyp (SEQ ID NO: 28)
RD()GTAT-Orn()-ATERLA-Aad-FLQRATF-Gly(Me)-A-Ile(Me)-LSSTEVGSNT-Hyp (SEQ ID NO: 29)
RD()GTAT-Orn()-ATERLA-Aad-FLQRAAF-Gly(Me)-A-Ile(Me)-LSSTEVGSNT-Hyp (SEQ ID NO: 30)
RD()GTAT-Orn()-ATERLA-Aad-FLQRGTF-Gly(Me)-A-Ile(Me)-LSSTEVGSNT-Hyp (SEQ ID NO: 31)
RD()QTAT-Orn()-ATERLA-Aad-FLQRGTF-Gly(Me)-A-Ile(Me)-LSSTEVGSNT-Hyp (SEQ ID NO: 32)
RD()PTATK()ATERLA-Aad-FLQRSSF-Gly(Me)-A-Ile(Me)-LSSTEVGSNT-Hyp (SEQ ID NO: 33)
ED()GTATK()ATERLA-Aad-FLQRSSF-Gly(Me)-A-Ile(Me)-PSSTEVGSNT-Hyp (SEQ ID NO: 34)
RD()GTATK()ATERLA-Aad-FLQRAAF-Gly(Me)-A-Ile(Me)-LSSTEVGSNT-Hyp (SEQ ID NO: 35)
RD()GTATK()ATERLA-Aad-FLQRGGF-Gly(Me)-A-Ile(Me)-LSSTEVGSNT-Hyp (SEQ ID NO: 36)
RD()GTATK()ATERLA-Aad-FLQRANF-Gly(Me)-A-Ile(Me)-LSSTEVGSNT-Hyp (SEQ ID NO: 37)
RD()GTATK()ATERLA-Aad-FLQRSSF-Gly(Me)-A-Ile(Me)-PSSTEVGSNT-Hyp (SEQ ID NO: 38)
RD()GTATK()ATERLA-Aad-FLQRSSF-Gly(Me)-A-Ile(Me)-LSSTEVGSNT-Hyp (SEQ ID NO: 39)
RD()GTATK()ATERLA-Aad-FLQRSSF-Gly(Me)-A-Ile(Me)-LSSTETGSNT-Hyp (SEQ ID NO: 40)
ED()GTATK()ATERLA-Aad-FLQRSSFGly(Me)-A-Ile(Me)-LSSTEVGSNT-Hyp (SEQ ID NO: 41)
RD()GTATK()ATERLA-Aad-FLQRTTF-Gly(Me)-A-Ile(Me)-LSSTEVGSNT-Hyp (SEQ ID NO: 42)
KD()GTATK()ATQRLA-Aad-FLQRSSF-Gly(Me)-A-Ile(Me)-LSSTEVGSNT-Hyp (SEQ ID NO: 43)
RD()GTATK()ATQRLA-Aad-FLQRSSF-Gly(Me)-A-Ile(Me)-LSSTEVGSNT-Hyp (SEQ ID NO: 44)
RD()GTATK()ATQRLADFLQRSSF-Gly(Me)-A-Ile(Me)-LSSTEVGSNT-Hyp

```
                                              (SEQ ID NO: 45)
RD()GTATK()ATQRLADFLQRSSF-Gly(Me)-A-
Ile(Me)-LSSTETGSNT-Hyp (SEQ ID NO: 46)
KD()GTATK()ATQRLANFLQRSSF-Gly(Me)-A-
Ile(Me)-LSSTEVGSNT-Hyp (SEQ ID NO: 47)
KD()GTATK()ATQRLANFLQRSSF-Gly(Me)-A-
Ile(Me)-LSSTETGSNT-Hyp (SEQ ID NO: 48)
R-Dap()-GTATD()ATERLAHFLQRSSF-Gly(Me)-A-
Ile(Me)-LSSTEVGSNT-Hyp (SEQ ID NO: 49)
R-Dab()-GTATD()ATERLAHFLQRSSF-Gly(Me)-A-
Ile(Me)-LSSTEVGSNT-Hyp (SEQ ID NO: 50)
R-Orn()-GTATD()ATERLAHFLQRSSF-Gly(Me)-A-
Ile(Me)-LSSTEVGSNT-Hyp (SEQ ID NO: 51)
R-Dap()-GTAT-Aad()-ATERLAHFLQRSSF-Gly(Me)-A-
Ile(Me)-LSSTEVGSNT-Hyp (SEQ ID NO: 52)
R-Dab()-GTATE()ATERLAHFLQRSSF-Gly(Me)-A-
Ile(Me)-LSSTEVGSNT-Hyp (SEQ ID NO: 53)
R-Aad()-GTAT-Dap()-ATERLAHFLQRSSF-Gly(Me)-A-
Ile(Me)-LSSTEVGSNT-Hyp (SEQ ID NO: 54)
RE()GTAT-Dab()-ATERLAHFLQRSSF-Gly(Me)-A-
Ile(Me)-LSSTEVGSNT-Hyp
``` or a pharmaceutically acceptable salt or solvate thereof.

The lactam bridge at positions 2 and 7 is indicated by parentheses ( ) following the residues at those positions.

In some embodiments, $R^1$ is M or M-L-, and/or $R^2$ is $NH_2$.

Specific compounds of the invention include:

```
(Compound 1)
                                              (SEQ ID NO: 55)
[19CD]-isoGlu-RD()GTAT-Dap()-ATERLAHFLQRSSF-
Gly(Me)-A-Ile(Me)-LSSTEVGSNT-Hyp-NH2

(Compound 2)
                                              (SEQ ID NO: 56)
[19CD]-isoGlu-RD()GTAT-Dab()-ATERLAHFLQRSSF-
Gly(Me)-A-Ile(Me)-LSSTEVGSNT-Hyp-NH2

(Compound 3)
                                              (SEQ ID NO: 57)
[19CD]-isoGlu-RD()GTAT-Orn()-ATERLAHFLQRSSF-
Gly(Me)-A-Ile(Me)-LSSTEVGSNT-Hyp-NH2

(Compound 4)
                                              (SEQ ID NO: 58)
[19CD]-isoGlu-isoGlu-RD()GTAT-Orn()-
ATERLAHFLQRSSF-Gly(Me)-A-Ile(Me)-
LSSTEVGSNT-Hyp-NH2

(Compound 5)
                                              (SEQ ID NO: 59)
[19CD]-isoGlu-RD()GTAT-Orn()-ATERLAHFLQRSSF-
Gly(Me)-A-Ile(Me)-PSSTEVGSNT-Hyp-NH2

(Compound 6)
                                              (SEQ ID NO: 60)
[19CD]-isoGlu-RD()GTAT-Orn()-ATERLAHFLQRF-
Gly(Me)-A-Ile(Me)-LSSTE-VGSNT-Hyp-NH2

(Compound 7)
                                              (SEQ ID NO: 61)
[19CD]-isoGlu-RD()GTAT-Orn()-ATERLAHFLHRSSF-
Gly(Me)-A-Ile(Me)-LSSTEVGSNTP-NH2

(Compound 8)
                                              (SEQ ID NO: 62)
[19CD]-isoGlu-RD()GTAT-Orn()-ATQRLAHFLQRSSF-
Gly(Me)-A-Ile(Me)-LSSTEVGSNT-Hyp-NH2

(Compound 9)
                                              (SEQ ID NO: 63)
[19CD]-isoGlu-RD()GTAT-Orn()-ATQRLAHFLQRSSF-
Gly(Me)-A-Ile(Me)-PSSTEVGSNT-Hyp-NH2

(Compound 10)
                                              (SEQ ID NO: 64)
[19CD]-isoGlu-RD()GTAT-Orn()-ATERLARFLQRSSF-
Gly(Me)-A-Ile(Me)-LSSTEVGSNT-Hyp-NH2

(Compound 11)
                                              (SEQ ID NO: 65)
[19CD]-isoGlu-ED()GTATK()ATERLAHFLQRSSF-
Gly(Me)-A-Ile(Me)-LSSTE-VGSNT-Hyp-NH2

(Compound 12)
                                              (SEQ ID NO: 66)
[19CD]-isoGlu-RD()GEATK()ATERLAHFLQRSSF-
Gly(Me)-A-Ile(Me)-LSSTE-VGSNT-Hyp-NH2

(Compound 13)
                                              (SEQ ID NO: 67)
[19CD]-isoGlu-RD()GTLTK()ATERLAHFLQRSSF-
Gly(Me)-A-Ile(Me)-LSSTE-VGSNT-Hyp-NH2

(Compound 14)
                                              (SEQ ID NO: 68)
[19CD]-isoGlu-RD()GTASK()ATERLAHFLQRSSF-
Gly(Me)-A-Ile(Me)-LSSTE-VGSNT-Hyp-NH2

(Compound 15)
                                              (SEQ ID NO: 69)
[19CD]-isoGlu-RD()GTATK()ATQRLAHFLQRSSF-
Gly(Me)-A-Ile(Me)-PSSTE-VGSNT-Hyp-NH2

(Compound 16)
                                              (SEQ ID NO: 70)
[19CD]-isoGlu-RD()GTATK()ATQRLAHFLQRSSF-
Gly(Me)-A-Ile(Me)-LSSTE-VGSNT-Hyp-NH2
```

(Compound 17)
(SEQ ID NO: 71)
[19CD]-isoGlu-RD()GTATK()ATERLAHFLQRSSF-Gly(Me)-A-Ile(Me)-PSSTE-VGSNT-Hyp-NH$_2$ (Compound 18)
(SEQ ID NO: 72)
[19CD]-isoGlu-RD()GTATK()ATERLAHFLQRSSF-Gly(Me)-A-Ile(Me)-LSSTE-VGSNT-Hyp-NH$_2$ (Compound 19)
(SEQ ID NO: 73)
[19CD]-isoGlu-RD()GTAT-hLys()-ATERLAHFLQRSSF-Gly(Me)-A-Ile(Me)-LSSTEVGSNT-Hyp-NH$_2$ (Compound 20)
(SEQ ID NO: 74)
[19CD]-isoGlu-RD()GTAT-Orn()-ATERLA-Aad-FLQRSSF-Gly(Me)-A-Ile(Me)-LSSTEVGSNT-Hyp-NH$_2$ (Compound 21)
(SEQ ID NO: 75)
[19CD]-isoGlu-RD()GTAT-Orn()-ATERLA-Aad-FLQRSSF-Gly(Me)-A-Ile(Me)-PSSTEVGSNT-Hyp-NH$_2$ (Compound 22)
(SEQ ID NO: 76)
[19CD]-isoGlu-RD()GTAT-Orn()-ATERLA-Aad-FLTRSSF-Gly(Me)-A-Ile(Me)-LSSTEVGSST-Hyp-NH$_2$ (Compound 23)
(SEQ ID NO: 77)
[19CD]-isoGlu-RD()GTAT-Orn()-ATERLA-Aad-FLQRTTF-Gly(Me)-A-Ile(Me)-LSSTEVGSNT-Hyp-NH$_2$ (Compound 24)
(SEQ ID NO: 78)
[19CD]-isoGlu-RD()GTAT-Orn()-ATERLA-Aad-FLQRTTF-Gly(Me)-A-Ile(Me)-PSSTEVGSNT-Hyp-NH$_2$ (Compound 25)
(SEQ ID NO: 79)
[19CD]-isoGlu-RD()GTAT-Orn()-ATERLA-Aad-FLQRATF-Gly(Me)-A-Ile(Me)-LSSTEVGSNT-Hyp-NH$_2$ (Compound 26)
(SEQ ID NO: 80)
[19CD]-isoGlu-RD()GTAT-Orn()-ATERLA-Aad-FLQRAAF-Gly(Me)-A-Ile(Me)-LSSTEVGSNT-Hyp-NH$_2$ (Compound 27)
(SEQ ID NO: 81)
[19CD]-isoGlu-RD()GTAT-Orn()-ATERLA-Aad-FLQRGTF-Gly(Me)-A-Ile(Me)-LSSTEVGSNT-Hyp-NH$_2$ (Compound 28)
(SEQ ID NO: 82)
[19CD]-isoGlu-RD()QTAT-Orn()-ATERLA-Aad-FLQRGTF-Gly(Me)-A-Ile(Me)-LSSTEVGSNT-Hyp-NH$_2$ (Compound 29)
(SEQ ID NO: 83)
[19CD]-isoGlu-RD()PTATK()ATERLA-Aad-FLQRSSF-Gly(Me)-A-Ile(Me)-LSSTEVGSNT-Hyp-NH$_2$ (Compound 30)
(SEQ ID NO: 84)
[19CD]-isoGlu-ED()GTATK()ATERLA-Aad-FLQRSSF-Gly(Me)-A-Ile(Me)-PSSTEVGSNT-Hyp-NH$_2$ (Compound 31)
(SEQ ID NO: 85)
[19CD]-isoGlu-RD()GTATK()ATERLA-Aad-FLQRAAF-Gly(Me)-A-Ile(Me)-LSSTEVGSNT-Hyp-NH$_2$ (Compound 32)
(SEQ ID NO: 86)
[19CD]-isoGlu-RD()GTATK()ATERLA-Aad-FLQRGGF-Gly(Me)-A-Ile(Me)-LSSTEVGSNT-Hyp-NH$_2$ (Compound 33)
(SEQ ID NO: 87)
[19CD]-isoGlu-RD()GTATK()ATERLA-Aad-FLQRANF-Gly(Me)-A-Ile(Me)-LSSTEVGSNT-Hyp-NH$_2$ (Compound 34)
(SEQ ID NO: 88)
[19CD]-isoGlu-RD()GTATK()ATERLA-Aad-FLQRSSF-Gly(Me)-A-Ile(Me)-PSSTEVGSNT-Hyp-NH$_2$ (Compound 35)
(SEQ ID NO: 89)
[19CD]-isoGlu-RD()GTATK()ATERLA-Aad-FLQRSSF-Gly(Me)-A-Ile(Me)-LSSTEVGSNT-Hyp-NH$_2$ (Compound 36)
(SEQ ID NO: 90)
[19CD]-isoGlu-RD()GTATK()ATERLA-Aad-FLQRSSF-Gly(Me)-A-Ile(Me)-LSSTETGSNT-Hyp-NH$_2$ (Compound 37)
(SEQ ID NO: 91)
[19CD]-isoGlu-ED()GTATK()ATERLA-Aad-FLQRSSF-Gly(Me)-A-Ile(Me)-LSSTEVGSNT-Hyp-NH$_2$ (Compound 38)
(SEQ ID NO: 92)
[19CD]-isoGlu-RD()GTATK()ATERLA-Aad-FLQRTTF-Gly(Me)-A-Ile(Me)-LSSTEVGSNT-Hyp-NH$_2$ (Compound 39)
(SEQ ID NO: 93)
[19CD]-isoGlu-KD()GTATK()ATQRLA-Aad-FLQRSSF-Gly(Me)-AIle(Me)-LSSTEVGSNTHyp-NH$_2$ (Compound 40)
(SEQ ID NO: 94)
[19CD]-isoGlu-RD()GTATK()ATQRLA-Aad-FLQRSSF-Gly(Me)-A-Ile(Me)-LSSTEVGSNT-Hyp-NH$_2$ (Compound 41)
(SEQ ID NO: 95)
[19CD]-isoGlu-RD()GTATK()ATQRLADFLQRSSF-Gly(Me)-A-Ile(Me)-LSSTE-VGSNT-Hyp-NH$_2$ (Compound 42)
(SEQ ID NO: 96)
[19CD]-isoGlu-RD()GTATK()ATQRLADFLQRSSF-Gly(Me)-A-Ile(Me)-LSSTETGSNT-Hyp-NH$_2$ -continued (Compound 43)
(SEQ ID NO: 97)
[19CD]-isoGlu-KD()GTATK()ATQRLANFLQRSSF- Gly(Me)-A-Ile(Me)-LSSTE-VGSNT-Hyp-NH$_2$ (Compound 44)
(SEQ ID NO: 98)
[19CD]-isoGlu-KD()GTATK()ATQRLANFLQRSSF- Gly(Me)-A-Ile(Me)-LSSTETGSNT-Hyp-NH$_2$ (Compound 45)
(SEQ ID NO: 99)
[19CD]-isoGlu-R-Dap()-GTATD()ATERLAHFLQRSSF- Gly(Me)-A-Ile(Me)-LSSTEVGSNT-Hyp-NH$_2$ (Compound 46)
(SEQ ID NO: 100)
[19CD]-isoGlu-R-Dab()-GTATD()ATERLAHFLQRSSF- Gly(Me)-A-Ile(Me)-LSSTEVGSNT-Hyp-NH$_2$ (Compound 47)
(SEQ ID NO: 101)
[19CD]-isoGlu-R-Orn()-GTATD()ATERLAHFLQRSSF- Gly(Me)-A-Ile(Me)-LSSTEVGSNT-Hyp-NH$_2$ (Compound 48)
(SEQ ID NO: 102)
[19CD]-isoGlu-R-Dap()-GTAT-Aad()-ATERLAHFLQRSSF- Gly(Me)-A-Ile(Me)-LSSTEVGSNT-Hyp-NH$_2$ (Compound 49)
(SEQ ID NO: 103)
[19CD]-isoGlu-R-Dab()-GTATE()ATERLAHFLQRSSF- Gly(Me)-A-Ile(Me)-LSSTEVGSNT-Hyp-NH$_2$ (Compound 50)
(SEQ ID NO: 104)
[19CD]-isoGlu-R-Aad()-GTAT-Dap()-ATERLAHFLQRSSF- Gly(Me)-A-Ile(Me)-LSSTEVGSNT-Hyp-NH$_2$ (Compound 51)
(SEQ ID NO: 105)
[19CD]-isoGlu-RE()GTAT-Dab()-ATERLAHFLQRSSF- Gly(Me)-A-Ile(Me)-LSSTEVGSNT-Hyp-NH$_2$ and pharmaceutically acceptable salts and solvates thereof.

The invention further provides a composition comprising an amylin analogue as described above. The composition may be a pharmaceutical composition, and may comprise a pharmaceutically acceptable carrier, excipient or vehicle.

The invention further provides a method for the synthesis of an amylin analogue as described above. The method may comprise the steps of synthesising the peptide by solid-phase or liquid-phase methodology, and optionally isolating and/or purifying the final product. The method may further comprise the step of forming an amide bond between the side chains at positions 2 and 7.

The present invention further provides an amylin analogue of the invention for use in a method of medical treatment.

The amylin analogues are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes), hypertension, dyslipidemia, sleep apnea and cardiovascular disease. The subject may be affected by obesity accompanied by at least one weight-related co-morbid condition, such as diabetes (e.g. type 2 diabetes), hypertension, dyslipidemia, sleep apnea and cardiovascular disease. It will be understood that the amylin analogues may thus be administered to subjects affected by conditions characterised by inadequate control of appetite or otherwise over-feeding, such as binge-eating disorder and Prader-Willi syndrome. It will be clear that the analogues can be used for treatment of combinations of the conditions described.

Thus, the invention provides an amylin analogue of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides an amylin analogue of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides an amylin analogue of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof.

The invention also provides an amylin analogue of the invention for use in a method of lowering circulating LDL levels and/or increasing HDL/LDL ratio.

Effects of amylin analogues on these conditions may be mediated in whole or in part via an effect on body weight, or may be independent thereof.

The invention further provides use of an amylin analogue of the invention in the manufacture of a medicament for treating, inhibiting or reducing weight gain, promoting weight loss and/or reducing excess body weight.

The invention also provides use of an amylin analogue of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides use of an amylin analogue of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof.

The invention also provides use of an amylin analogue of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of an amylin analogue of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of an amylin analogue of the invention to the subject. The subject may be affected by obesity accompanied by at least one weight-related co-morbid condition, such as diabetes (e.g. type 2 diabetes), hypertension, dyslipidemia, sleep apnea and cardiovascular disease.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication), coronary heart disease, peripheral artery disease or stroke, and combinations thereof, in a subject, comprising administering a therapeutically effective amount of an amylin analogue of the invention to the subject.

The invention further provides a method of lowering circulating LDL levels and/or increasing HDL/LDL ratio in a subject, comprising administering a therapeutically effective amount of an amylin analogue of the invention to the subject.

The invention further provides the use of an amylin analogue as described above in a method of cosmetic (i.e. non-therapeutic) weight loss. It will be understood that references to therapeutic uses of amylin analogues and methods comprising administration of amylin analogues may equally be taken to encompass uses and administration of such compositions.

Further aspects and embodiments of the present invention will become apparent from the disclosure below.

DETAILED DESCRIPTION OF THE INVENTION

Unless otherwise defined herein, scientific and technical terms used herein shall have the meanings that are commonly understood by those of ordinary skill in the art. Generally, nomenclature employed herein in connection with techniques of chemistry, molecular biology, cell and cancer biology, immunology, microbiology, pharmacology, and protein and nucleic acid chemistry, described herein, is that well known and commonly used in the art.

All publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer or component, or of a stated group of integers or components, but not the exclusion of any other integer or component or group of integers or components.

The singular forms "a," "an," and "the" include the plurals unless the context clearly dictates otherwise.

The term "including" is used to mean "including but not limited to." "Including" and "including but not limited to" are used interchangeably.

The terms "patient", "subject," and "individual" may be used interchangeably and may refer to either a human or a non-human animal. Subjects are typically mammals, including humans, non-human primates (including great apes, Old World monkeys and New World monkeys), livestock animals (e.g., bovines, porcines), companion animals (e.g., canines, felines) and rodents (e.g., mice and rats).

As used herein, the term "pharmaceutically acceptable salt" is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", $3^{rd}$ edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide or pharmaceutically acceptable salt thereof according to the invention) and a solvent. The solvent in this connection may, for example, be water, ethanol or another pharmaceutically acceptable—typically small-molecular—organic species, such as, but not limited to, acetic acid or lactic acid. When the solvent in question is water, such a solvate is normally referred to as a hydrate.

The term "agonist" as employed in the context of the invention refers to a substance that activates the receptor type in question, typically by binding to it (i.e. as a ligand).

Each embodiment of the invention described herein may be taken alone or in combination with one or more other embodiments of the invention.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of certain less common or non-naturally occurring amino acids (i.e. amino acids other than the 20 encoded by the standard mammalian genetic code), unless they are referred to by their full name (e.g. sarcosine, ornithine, etc.), frequently employed three- or four-character codes are employed for residues thereof, including Orn (ornithine, i.e. 2,5-diaminopentanoic acid), Aib (α-aminoisobutyric acid), Dab (2,4-diaminobutanoic acid), Dap (2,3-diaminopropanoic acid), Har (homoarginine), γ-Glu (γ-glutamic acid), Gaba (γ-aminobutanoic acid), β-Ala (i.e. 3-aminopropanoic acid), 8Ado (8-amino-3,6-dioxaoctanoic acid).

Unless otherwise indicated, reference is made to the L-isomeric forms of the amino acids in question.

Additional abbreviations include the following:

Gly(Me): N-methylglycine [also known as sarcosine (Sar)]

Ile(Me): N-methylisoleucine

Aad: 2-aminoadipic acid, e.g. (2S)-2-aminoadipic acid [also (2S)-2-aminohexanedioic acid], also known as homoglutamic acid Hyp: 4-hydroxyproline, e.g. (2S,4R)-4-hydroxyproline [also denoted (4R)-4-hydroxy-L-proline]

Dap: 2,3-diaminopropanoic acid, e.g. (2S)-2,3-diaminopropanoic acid

Dab: 2,4-diaminobutanoic acid, e.g. (2S)-2,4-diaminobutanoic acid hLys: 2-amino-7-amino-heptanoic acid, also known as homo-lysine, e.g. (2S)-2-amino-7-amino-heptanoic acid The term "therapeutically effective amount" as used herein in the context of the above-described methods of treatment or other therapeutic interventions according to the invention refers to an amount that is sufficient to cure, ameliorate, alleviate or partially arrest the clinical manifestations of the particular disease, disorder or condition that is the object of the treatment or other therapeutic intervention in question e.g. as measured by established clinical endpoints or other biomarkers (established or experimental). A therapeutically relevant amount may be determined empirically by one skilled in the art based on the indication being treated or prevented and the subject to whom the therapeutically relevant amount is being administered. For example, the skilled worker may measure one or more of the clinically relevant indicators of bioactivity described herein, e.g. plasma lipid levels, blood glucose levels or insulin release. The skilled worker may determine a clinically relevant amount through in vitro or in vivo measurements. Other exemplary measures include weight gain, weight loss, and change in blood pressure.

An amount adequate to accomplish any or all of these effects is defined as a therapeutically effective amount. The administered amount and the method of administration can be tailored to achieve optimal efficacy. An amount effective for a given purpose will depend, inter alia, on the severity of the disease, disorder or condition that is the object of the particular treatment or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide or pharmaceutically acceptable salt or solvate thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. weight gain or hyperglycemia) relative to the absence of treatment, and is not necessarily meant to imply complete cessation of the relevant disease, disorder or condition.

The terms "prevention" and grammatical variants thereof (e.g., "prevented", "preventing", "prevent") as employed in the present context refer to an approach for hindering or preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of "prevention" may thus be a subject not yet afflicted with the disease or disorder in question. The term "prevention" thus includes inhibiting or slowing the onset of disease relative to the absence of treatment, and is not necessarily meant to imply permanent prevention of the relevant disease, disorder or condition.

Synthesis of Amylin Analogues

The invention further provides a method of synthesis of an amylin analogue of the invention. The amylin analogues (which may also be referred to as compounds or peptides) may suitably be manufactured by standard synthetic methods. Thus, the peptides may be synthesized by, e.g., methods comprising synthesizing the peptide by standard solid-phase or liquid-phase methodology, either stepwise or by fragment assembly, and optionally isolating and purifying the final peptide product. In this context, reference may be made to WO 98/11125 or, inter alia, Fields, G. B. et al., "Principles and Practice of Solid-Phase Peptide Synthesis"; in: *Synthetic Peptides*, Gregory A. Grant (ed.), Oxford University Press (2$^{nd}$ edition, 2002) and the synthesis examples herein. The method typically further comprises the step of forming an amide bond between the side chains at positions 2 and 7, e.g. as described below. In the case of solid phase synthesis, cyclisation may be performed in situ on the solid phase (e.g. resin), i.e. before removal of the peptide from the solid phase.

$C_{1-4}$ Acyl Groups $C_{1-4}$ acyl groups that may be present as a group $R^1$ in the context of compounds of the present invention include formyl (i.e. methanoyl), acetyl (i.e. ethanoyl), propanoyl, 1-butanoyl and 2-methylpropanoyl groups.

$C_{1-4}$ Alkyl Groups $C_{1-4}$ alkyl groups that may be present as a group $R^1$ in the context of compounds of the present invention include, but are not limited to, $C_{1-3}$ alkyl groups, such as methyl, ethyl, 1-propyl or 2-propyl.

$C_{1-3}$ Alkyl Groups $C_{1-3}$ alkyl groups that may be present as a group $R^3$ in the context of compounds of the present invention include methyl, ethyl, 1-propyl and 2-propyl.

Half-Life Extending Moieties M

As described herein, the N-terminal moiety $R^1$ in a compound of the invention may be a half-life extending moiety M (sometimes referred to in the literature as, inter alia, a duration enhancing moiety or albumin binding moiety), optionally linked (covalently attached) to the peptide moiety Z via a linker moiety L. Among suitable half-life extending moieties are certain types of lipophilic substituents. Without wishing to be bound by any particular theory, it is thought that such lipophilic substituents (and other classes of half-life extending moieties) bind albumin in the blood stream, thereby shielding the compound of the invention from renal filtration as well as enzymatic degradation and thus possibly enhancing the half-life of the compound in vivo. The lipophilic substituent may also modulate the potency of the compound as an agonist to the amylin (calcitonin) receptor.

The lipophilic substituent may be attached to the N-terminal amino acid residue or to the linker L via an ester, a sulfonyl ester, a thioester, an amide, an amine or a sulfonamide. Accordingly it will be understood that preferably the lipophilic substituent includes an acyl group, a sulfonyl group, an N atom, an O atom or an S atom which forms part of the ester, sulfonyl ester, thioester, amide, amine or sulfonamide. Preferably, an acyl group in the lipophilic substituent forms part of an amide or ester with the amino acid residue or the linker.

The lipophilic substituent may comprise a hydrocarbon chain having from 10 to 24 C atoms, e.g. from 14 to 22 C atoms, e.g. from 16 to 20 C atoms. Preferably it has at least 14 C atoms, and preferably has 20 C atoms or fewer. For example, the hydrocarbon chain may contain 14, 15, 16, 17, 18, 19 or 20 carbon atoms. The hydrocarbon chain may be linear or branched, and may be saturated or unsaturated. Furthermore, it can include a functional group at the end of the hydrocarbon chain, e.g. a carboxylic acid group which may or may not be protected during synthesis. From the discussion above it will also be understood that the hydrocarbon chain is preferably substituted with a moiety which forms part of the attachment to the N-terminal amino acid residue of the peptide moiety Z or to the linker L, for example an acyl group, a sulfonyl group, an N atom, an O atom or an S atom.

Most preferably, the hydrocarbon chain is substituted with an acyl group, and accordingly the hydrocarbon chain may be part of an alkanoyl group, for example a dodecanoyl, 2-butyloctanoyl, tetradecanoyl, hexadecanoyl, heptadecanoyl, octadecanoyl, nonadecanoyl or eicosanoyl group. Examples of functionalized hydrocarbon chains are 15-carboxy-pentadecanoyl, 17-carboxy-heptadecanoyl and 19-carboxy-nonadecanoyl.

As mentioned above, a lipophilic substituent M may be linked to the N-terminal amino acid residue of Z via a linker L. In embodiments, the linker moiety L may itself comprise one, two, three or more linked sub-moieties $L^1$, $L^2$, $L^3$, . . . etc. When the linker L comprises only one such moiety, it is attached to the lipophilic substituent and to the N-terminal amino acid residue of Z. The linker may then be attached to the lipophilic substituent and to the N-terminal amino acid residue of Z independently by means of an ester, a sulfonyl ester, a thioester, an amide, an amine or a sulfonamide bond. Accordingly, it may include two moieties independently selected from acyl, sulfonyl, an N atom, an O atom and an S atom. The linker may consist of a linear or branched $C_{1-10}$ hydrocarbon chain or more preferably a linear $C_{1-5}$ hydrocarbon chain. Furthermore the linker can be substituted with one or more substituents selected from $C_{1-6}$ alkyl, amino $C_{1-6}$ alkyl, hydroxy $C_{1-6}$ alkyl and carboxy $C_{1-6}$ alkyl.

In some embodiments the linker may comprise one or more (e.g. one, two or three) linked amino acid residues, which may each independently be a residue of any naturally occurring or non-naturally occurring amino acid. For example, the linker may comprise one, two or three linked amino acid residues, each of which may independently be a residue of Gly, Pro, Ala, Val, Leu, Ile, Met, Cys, Phe, Tyr, Trp, His, Lys, Arg, Gln, Asn, α-Glu, γ-Glu, ε-Lys, Asp, β-Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8Ado (i.e. 8-amino-3,6-dioxaoctanoyl).

References to γ-Glu, ε-Lys, and β-Asp indicate residues of amino acids which participate in bonds via their side chain carboxyl or amine functional groups. Thus γ-Glu, and β-Asp participate in bonds via their alpha amino and side chain carboxyl groups, while ε-Lys participates via its carboxyl and side chain amino groups. In the context of the present invention, γ-Glu and isoGlu are used interchangeably.

In certain embodiments, the linker comprises or consists of one, two or three independently selected residues of Glu, γ-Glu, ε-Lys, β-Ala, 4-aminobutanoyl, 8-aminooctanoyl or 8Ado.

Linkers consisting of isoGlu and isoGlu-isoGlu may be particularly preferred.

An example of a lipophilic substituent comprising a lipophilic moiety M and linker L is shown in the formula below:

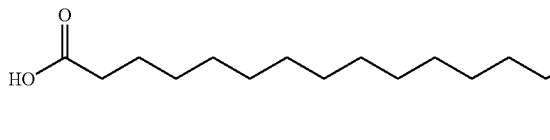

Here, the backbone nitrogen of an Arg residue (present at position X1 of the amylin analogue's peptide sequence Z) is covalently attached to the side chain carboxyl group of a Glu moiety via an amide linkage. A 19-carboxy-nonadecanoyl group is covalently attached to the alpha amino group of the Glu linker via an amide linkage. Thus the Glu linker is in an iso-Glu (or γ-Glu) configuration. This combination of lipophilic moiety and linker, attached to an Arg residue, may be referred to by the shorthand notation [19CD]-isoGlu-R, e.g. when shown in formulae of specific compounds.

The skilled person will be well aware of suitable techniques for preparing the compounds employed in the context of the invention. For examples of suitable chemistry, see, e.g., WO98/08871, WO00/55184, WO00/55119, Madsen et al (*J. Med. Chem.* 2007, 50, 6126-32), and Knudsen et al. 2000 (*J. Med Chem.* 43, 1664-1669).

The hydrocarbon chain in a lipophilic substituent may be further substituted. For example, it may be further substituted with up to three substituents selected from $NH_2$, OH and COOH. If the hydrocarbon chain is further substituted, it is preferably further substituted with only one substituent. Alternatively or additionally, the hydrocarbon chain may include a cycloalkane or heterocycloalkane moiety, for example as shown below:

In some embodiments, the cycloalkane or heterocycloalkane moiety is a six-membered ring, e.g. a piperidine ring.

In alternative embodiments of the present invention, the N-terminal amino acid of Z in a compound of the invention may be linked (covalently attached) to a biotinylic substituent, optionally via a linker moiety L. Without wishing to be bound by any particular theory, it is likewise believed that such biotinylic substituents bind to albumin in the blood stream, thereby shielding the compound of the invention from enzymatic degradation and thus possibly enhancing the half-life of the compound in vivo. A linker, when present, may provide spacing between the peptide moiety Z and the biotinylic substituent.

The biotinylic substituent may be attached to the N-terminal amino acid residue or to the linker via an maleimide ester bond, a sulfonyl ester bond, a thioester bond, an amide bond, an amine bond or a sulfonamide bond. Accordingly it will be understood that the biotinylic substituent preferably comprises an maleimido group, an acyl group, a sulfonyl group, an N atom, an O atom or an S atom which forms part of the ester, sulfonyl ester, thioester, amide, amine or sulfonamide bond in question.

Examples of biotinylic substituents may include

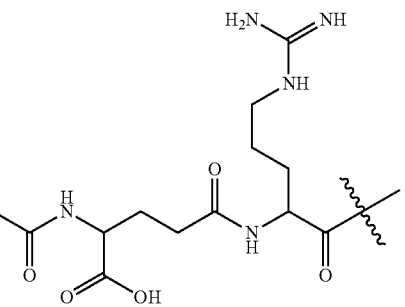

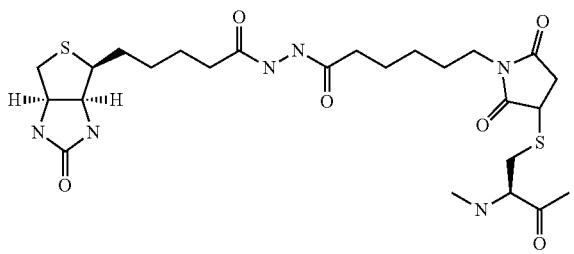 [SMILES: CN[C@@H](CSC1CC(=O)N(CCCCCC(=O)NNC(=O)CCCC[C@@H]2SC[C@@H]3NC(=O)N[C@@H]32)C1=O)C(C)=O]

Biotin is known as Vitamin H or Coenzyme R, and is a water-soluble B-complex vitamin (vitamin B7). It has been shown to increase oral uptake of certain drugs.

Efficacy of Compounds

The compounds of the invention are amylin receptor agonists, i.e. they are capable of binding to, and inducing signaling by, one or more receptors or receptor complexes regarded as physiological receptors for human amylin. These include the human calcitonin receptor hCT-R, as well as complexes comprising the human calcitonin receptor hCT-R and at least one of the human receptor activity modifying proteins designated hRAMP1, hRAMP2 and hRAMP3. Complexes between hCT-R and hRAMP1, hRAMP2 and hRAMP3 are designated hAMYR1, hAMYR2 and hAMYR3 (i.e. human amylin receptors 1, 2 and 3) respectively.

Without wishing to be bound by theory, a compound may be considered an amylin receptor agonist if it has agonist activity at one or more of hAMYR1, hAMYR2 and hAMYR3, e.g. against hAMYR1 and/or hAMYR3, e.g. at hAMYR3.

Typically an amylin receptor agonist will also have agonist activity at hCT-R when expressed in the absence of hRAMP1, hRAMP2 and hRAMP3. Typically, the agonist will have activity at hCT-R (when expressed in the absence of hRAMP1, hRAMP2 and hRAMP3) which is less than 10-fold higher than its activity at any one of hAMYR1, hAMYR2 and hAMYR3 (i.e. its activity at all of these receptors) in a comparable assay. Agonist activity at hCT-R may be less than 5-fold higher than agonist activity at hAMYR1, hAMYR2 and hAMYR3, substantially equal to (e.g. +/−10%) agonist activity at hAMYR1, hAMYR2 and hAMYR3, or less than agonist activity at hAMYR1, hAMYR2 and hAMYR3. In this regard, it may be sufficient just to compare activity between hCT-R and hAMYR3.

The ability to induce cAMP formation (i.e. to induce adenylate cyclase activity) as a result of binding to the relevant receptor or receptor complex is typically regarded as indicative of agonist activity. Other intracellular signaling pathways or events may also be used as read-outs for amylin receptor agonist activity. These may include calcium release, β-arrestin recruitment, receptor internalization, kinase activation or inactivation, lipase activation, inositol phosphate release, diacylglycerol release or nuclear transcription factor translocation.

A suitable comparable assay format would utilize cells which express hCT-R and which differ only in their expression of hRAMP1, 2 and 3. For example, a "base" cell line which does not express any of hCT-R, hRAMP1, hRAMP2 and hRAMP3 may be engineered to generate cells which express (i) hCT-R, and (ii) one of hAMYR1, hAMYR2 and hAMYR3 (i.e. hCT-R plus one of hRAMP1, hRAMP2 and hRAMP3), e.g. hAMYR3. The base cells will typically be mammalian cells and may be primate cells. They may be non-human primate cells. Preferably the base cell does not express any of CT-R, RAMP1, RAMP2 or RAMP5 (whether human, or native to the base cell if the base cell is non-human). The base cells may be fibroblast cells. Suitable non-human fibroblast base cells include COS7 cells, from African green monkey, which do not express native CT-R or RAMPs.

Comparative activity may be measured by any suitable means, such as via determination of $EC_{50}$ values as described below. It will be apparent that the same biological read-out must be for both receptor types.

Compounds of the present invention may exhibit a number of advantageous properties in relation to human amylin and existing analogues thereof, such as pramlintide, IAPP-GI, and analogues described in WO2012/168430, WO2012/168431 and WO2012/168432. As compared to human amylin or any of those analogues, compounds of the invention may, for example, exhibit improved efficacy (e.g., in the form of improved in vitro activity or potency at one or more of the receptors hCT-R, hAMYR1, hAMYR2 or hAMYR3. Additionally or alternatively, compounds of the invention may exhibit improved solubility in aqueous media, especially at pH values in the range from 4 to 7.5, or at a range of pH values across that range. Moreover, compounds of the present invention may additionally or alternatively exhibit reduced tendency to undergo fibrillation in pharmaceutically relevant aqueous media, especially at pH values in the range from 4 to 7, or at a range of pH values across that range. Furthermore, compounds of the present invention may additionally or alternatively exhibit improved chemical stability (i.e. reduced tendency to undergo chemical degradation) in aqueous media, especially at pH values in the range from 4 to 9, or at a range of pH values across that range.

Compounds of the invention may thus be well suited for formulation in acidic media (e.g. pH 4) and in neutral or near-neutral media (e.g. pH 7 or 7.4). In contrast to pramlintide, for example, which generally exhibits poor chemical stability and rapid fibrillation in pharmaceutically relevant aqueous media at neutral pH, compounds of the invention may be thus well suited for co-formulation with, for example, insulin, various insulin analogues and/or other therapeutic (e.g. anti-diabetic or anti-obesity) agents that require a neutral or near-neutral formulation pH.

In general it is preferred to use a biological assay which measures intracellular signalling caused by binding of the compound to the relevant receptor, as discussed above. Activation of the calcitonin/amylin receptor by compounds of the invention (which behave as agonists of the receptor) induces cAMP formation and activation of other intracellular signaling pathways and events. Thus, production of cAMP or any other suitable parameter in suitable cells expressing the receptor can be used to monitor agonist activity towards the receptor.

The skilled person will be aware of suitable assay formats, and examples are provided below. For example, the assays may make use of the human calcitonin receptor (hCT-R, .e.g. isoform 2 of the hCT-R) or the hAMYR3 receptor (see the examples below). Where sequences of precursor proteins are referred to, it should be understood that assays may make use of the mature protein, lacking the signal sequence.

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$ [hCT-R] lower than the $EC_{50}$ [hCT-R] of native human amylin, or lower than that of pramlintide, in a particular assay may be considered to have higher potency or activity at the receptor than native human amylin, or higher than that of pramlintide, respectively.

In some embodiments of compounds of the present invention, the $EC_{50}$ towards hCT-R is below 1.5 nM (e.g. 0.001 to 1.5 nM).

In some embodiments of compounds of the present invention, the $EC_{50}$ towards hCT-R is below 0.9 nM (e.g. 0.001 to 0.9 nM).

In some embodiments of compounds of the present invention, the $EC_{50}$ towards hCT-R is below 0.5 nM (e.g. 0.001 to 0.5 nM).

In some embodiments of compounds of the present invention, the $EC_{50}$ towards hCT-R is below 0.3 nM (e.g. 0.001 to 0.3 nM).

In some embodiments of compounds of the present invention, the $EC_{50}$ towards hCT-R is below 0.2 nM (e.g. 0.001 to 0.2 nM).

The $EC_{50}$ at hCT-R may be an indication of the effect of a compound on food intake, weight gain and/or weight loss. Compounds with lower $EC_{50}$ values at hCT-R may have a greater effect on these parameters.

In some embodiments of compounds of the present invention, the $EC_{50}$ towards hAMYR3 is below 1.0 nM (e.g. 0.001 to 1.0 nM).

In some embodiments of compounds of the present invention, the $EC_{50}$ towards hAMYR3 is below 0.5 nM (e.g. 0.001 to 0.5 nM).

In some embodiments of compounds of the present invention, the $EC_{50}$ towards hAMYR3 is below 0.4 nM (e.g. 0.001 to 0.4 nM).

In some embodiments of compounds of the present invention, the $EC_{50}$ towards hAMYR3 is below 0.3 nM (e.g. 0.001 to 0.3 nM).

In some embodiments of compounds of the present invention, the $EC_{50}$ towards hAMYR3 is below 0.2 nM (e.g. 0.001 to 0.2 nM).

The $EC_{50}$ at hCT-R (when expressed in the absence of hRAMP1, hRAMP2 and hRAMP3) may be less than the $EC_{50}$ at any or all of hAMYR1, hAMYR2 and hAMYR3, e.g. at hAMYR3.

For example, the $EC_{50}$ at hCT-R (when expressed in the absence of hRAMP1, hRAMP2 and hRAMP3) may be less than 10-fold lower than the $EC_{50}$ at any or all of hAMYR1, hAMYR2 and hAMYR3, e.g. at hAMYR3.

The $EC_{50}$ at hCT-R (when expressed in the absence of hRAMP1, hRAMP2 and hRAMP3) may be less than 5-fold lower than the $EC_{50}$ at any or all of hAMYR1, hAMYR2 and hAMYR3, e.g. at hAMYR3.

The $EC_{50}$ at hCT-R (when expressed in the absence of hRAMP1, hRAMP2 and hRAMP3) may be substantially equal to (e.g. +/−50%) the $EC_{50}$ at any or all of hAMYR1, hAMYR2 and hAMYR3, e.g. at hAMYR3.

The $EC_{50}$ at hCT-R (when expressed in the absence of hRAMP1, hRAMP2 and hRAMP3) may be higher than the $EC_{50}$ at any or all of hAMYR1, hAMYR2 and hAMYR3, e.g. at hAMYR3.

Such assays may be performed under the conditions described in Example 2 below.

Additionally or alternatively, compounds of the invention may show excellent resistance to fibrillation. For example, they may show no detectable fibrillation after 96 hours at pH 4.0 and/or pH 7.0, e.g. at 40° C., e.g. under the conditions described in Example 4.

Additionally or alternatively, compounds of the invention may show excellent chemical stability, i.e. resistance to degradation in solution. For example, they may retain at least 70% purity, at least 75% purity, at least 80% purity, at least 85% purity, at least 90% purity, or at least 95% purity after incubation at pH 4, pH 6, and/or pH 7 at 40° C. for 72 hours, or for 14 days, e.g. under the conditions described in Example 5.

Therapeutic Uses

The compounds of the invention are useful, inter alia, in the reduction of food intake, promotion of weight loss, and inhibition or reduction of weight gain. They may therefore provide an attractive treatment option for, inter alia, obesity and metabolic diseases caused, characterised by, or associated with, excess body weight.

Thus, the compounds may be used in a method of treating, inhibiting or reducing weight gain, promoting weight loss, reducing food intake, and/or reducing excess body weight. Treatment may be achieved, for example, by control of appetite, feeding, food intake, calorie intake and/or energy expenditure.

The compounds may be used in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The compounds may also be used in in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart disease (including diabetic cardiomyopathy and heart failure as a diabetic complication) coronary heart disease, peripheral artery disease or stroke.

The compounds may also be useful in lowering circulating LDL levels and/or increasing HDL/LDL ratio.

The effects of the compounds described above may be mediated in whole or in part via an effect on body weight, or may be independent thereof.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with metabolic syndrome are at increased risk of coronary heart disease and other diseases related to other manifestations of arteriosclerosis (e.g. stroke and peripheral vascular disease). The dominant underlying risk factor for this syndrome appears to be abdominal obesity.

Pharmaceutical Compositions

The invention also extends to compositions, such as pharmaceutical compositions, comprising amylin analogues. As with all aspects of the invention, it is to be understood that reference to an amylin analogue encompasses reference to pharmaceutically acceptable salts and solvates.

The amylin analogues of the present invention may be formulated as pharmaceutical compositions which are suited for administration with or without storage, and which typically comprise a therapeutically effective amount of at least one peptide of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, PA, USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intravitreal, rectal, vaginal, nasal, topical, enteral or parenteral (including subcutaneous (sc), intramuscular (im), intravenous (iv), intradermal and transdermal) administration or administration by inhalation. The formulations may conveniently be presented in unit dosage form and may be prepared by any of the methods well known in the art of pharmaceutical formulation.

Subcutaneous or transdermal modes of administration may in some cases be suitable for peptides of the invention.

Further embodiments relate to devices, dosage forms and packages used to deliver the pharmaceutical formulations of the present invention. Thus, at least one peptide in a stable or preserved formulation or solution described herein can be administered to a patient in accordance with the present invention via a variety of delivery methods, including by sc or im injection, or by transdermal, pulmonary or transmucosal administration, or by implant, or by use of an osmotic pump, cartridge, micro-pump or other means recognized by a person of skill in the art.

Still further embodiments relate to oral formulations and oral administration. Formulations for oral administration may rely on the co-administration of adjuvants (e.g. resorcinols and/or nonionic surfactants such as polyoxyethylene oleyl ether and n-hexadecylpolyethylene ether) to artificially increase the permeability of the intestinal walls, and/or the co-administration of enzymatic inhibitors (e.g. pancreatic trypsin inhibitors, diisopropylfluorophosphate (DFF) or trasylol) to inhibit enzymatic degradation. The active constituent compound of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g. an inactive diluting agent, a lubricant (such as magnesium stearate), a paraben, a preserving agent (such as sorbic acid, ascorbic acid or alpha-tocopherol), an antioxidant (such as cysteine), a disintegrant, binder, thickener, buffering agent, pH-adjusting agent, sweetening agent, flavoring agent or perfuming agent.

Dosages

A typical dosage of an amylin analogue as employed in the context of the present invention may be in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. The exact dosage employed will depend, inter alia, on: the nature and severity of the disease or disorder to be treated, on the sex, age, body weight and general condition of the subject to be treated, on possible other, concomitant, disease or disorder that is undergoing or is to undergo treatment, as well as on other factors that will be known to a medical practitioner of skill in the art.

An amylin analogue of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like. Such regular peptide administration regimens may, in certain circumstances such as, e.g., during chronic long-term administration, be advantageously interrupted for a period of time so that the medicated subject reduces the level of, or stops taking, the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering peptides of the invention.

Thus, the peptide may be delivered via an administration regime which comprises two or more administration phases separated by respective drug holiday phases.

During each administration phase, the peptide is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the peptide to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the peptide.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of a possible following drug holiday phase is longer than the dosing interval used in that administration pattern. Where the dosing interval is irregular, the duration of a drug holiday phase may be greater than the mean interval between doses over the course of the administration phase. Alternatively the duration of the drug holiday may be longer than the longest interval between consecutive doses during the administration phase.

The duration of a possible drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime entailing the use of drug holiday comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a peptide of the invention, then typically the same combination of drugs or active agents is given in consecutive administration phases. In certain embodiments, the recipient subject is a human.

Combination Therapy

An amylin analogue of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a peptide of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™)

Moreover, a peptide of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802), Orlistat™, Sibutramine™, phentermine, a melanin concentrating hormone receptor 1 antagonist, CCK, amylin, pramlintide and leptin, as well as analogues thereof.

A peptide of the invention may further be used in combination with an anti-hypertension agent of a known type, including, but not limited to, an angiotensin-converting enzyme inhibitor, an angiotensin II receptor blocker, a diuretic, a beta-blocker or a calcium channel blocker.

A peptide of the invention may still further be used in combination with an anti-dyslipidemia agent of known type, including, but not limited to, a statin, a fibrate, a niacin, a PSCK9 (Proprotein convertase subtilisin/kexin type 9) inhibitor, or a cholesterol absorption inhibitor.

A peptide of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™, Rabeprazole™, Zolpidem™, Alpidem™, Saripidem™ or Necopidem™.

In addition, with regard to anti-inflammatory treatment, a peptide of the invention may be beneficial if administered in combination with an anti-inflammatory agent of known type, including, but not limited to:

steroids and corticosteroids, such as beclomethasone, methylprednisolone, betamethasone, prednisone, dexamethasone, and hydrocortisone;

non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1b);

and certain other compounds, such as 5-aminosalicylic acid and prodrugs and pharmaceutically acceptable salts thereof.

Metformin has also been demonstrated to have anti-inflammatory properties (see, e.g., Haffner et al., *Diabetes* 54: 1566-1572 (2005)) and as such may also be useful in combination with compounds (peptides) of the invention.

Devices and Kits

In some embodiments, the invention relates to a device comprising an amylin analogue or pharmaceutical composition of the invention, for delivery of the analogue to a subject. Via such devices, amylin analogues can be administered to a patient via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising an amylin analogue of the invention or a pharmaceutical composition of the invention. In certain embodiments, the kit further comprises packaging and/or instructions for use.

The device or kit may be useful for combination therapy as described above. Thus the device or kit may further comprise a further active agent, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent as described above, or a pharmaceutical composition comprising such an active agent.

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed as limiting the scope of the present invention in any way.

Abbreviations Employed in the Examples Include:
Acm: acetaminomethyl
Alloc: allyloxycarbonyl
Boc: tert-butoxycarbonyl
BSA: bovine serum albumin
cAMP: cyclic adenosine monophosphate
COMU™: (1-cyano-2-ethoxy-2-oxoethylidenaminooxy) dimethylamino-morpholino-carbenium hexafluorophosphate
DCM: dichloromethane
DIPEA: diisopropylethylamine
DMEM: Dulbecco's Modified Eagle Medium
DMF: N,N-dimethylformamide
DODT: 3,6-dioxa-1,8-octanedithiol
ESI-MS: electron spray ionization mass spectrometry
EtOH: ethanol
$Et_2O$: diethyl ether
FCS: fetal calf serum
Fmoc: 9-fluorenylmethoxycarbonyl
HATU: 2-(7-aza-1H-benzotriazole-1-yl)-1,1,3,3-tetramethyluronium hexafluorophosphate
HEPES: N-2-hydroxyethylpiperazine-N'-2-ethanesulfonic acid
HPLC: high performance liquid chromatography
IBMX: 3-isobutyl-1-methylxanthine
MeCN: acetonitrile
MS: mass spectrometry
NEP: N-ethylpyrrolidone
NMP N-methylpyrrolidone
OAll: allylester
PBS: phosphate-buffered saline
p-ERK: phosphorylated extracellular regulated kinase
RP-HPLC: reverse phase high performance liquid chromatography
TFA: trifluoroacetic acid
TIS: triisopropylsilane
Trt: trityl (i.e. triphenylmethyl)
v/v: volume/volume
w/v: weight/volume The following examples are provided to illustrate certain embodiments of the invention and are not intended to limit the scope of the invention.

Measurement of Physiological Parameters

Unless otherwise specified, whole-blood glucose levels were determined on tail-vein blood samples by the Biosen (EKF Diagnostic, Germany) enzyme-based electrode method. Blood samples were analyzed for glycated hemoglobin (HbA1c) using a Cobas c111 analyzer (Roche Diagnostics, Mannheim, Germany).

Example 1: Synthesis of Compounds

The following compounds were synthesised:

(Compound 1)
(SEQ ID NO: 55)
[19CD]-isoGlu-RD()GTAT-Dap()-ATERLAHFLQRSSF-
Gly(Me)-A-Ile(Me)-LSSTEVGSNT-Hyp-$NH_2$ (Compound 2)
(SEQ ID NO: 56)
[19CD]-isoGlu-RD()GTAT-Dab()-ATERLAHFLQRSSF-
Gly(Me)-A-Ile(Me)-LSSTEVGSNT-Hyp-$NH_2$ (Compound 3)
(SEQ ID NO: 57)
[19CD]-isoGlu-RD()GTAT-Orn()-ATERLAHFLQRSSF-
Gly(Me)-A-Ile(Me)-LSSTEVGSNT-Hyp-$NH_2$ (Compound 4)
(SEQ ID NO: 58)
[19CD]-isoGlu-isoGlu-RD()GTAT-Orn()-
ATERLAHFLQRSSF-Gly(Me)-A-Ile(Me)-
LSSTEVGSNT-Hyp-$NH_2$ (Compound 5)
(SEQ ID NO: 59)
[19CD]-isoGlu-RD()GTAT-Orn()-ATERLAHFLQRSSF-
Gly(Me)-A-Ile(Me)-PSSTEVGSNT-Hyp-$NH_2$ (Compound 6)
(SEQ ID NO: 60)
[19CD]-isoGlu-RD()GTAT-Orn()-ATERLAHFLQRF-
Gly(Me)-A-Ile(Me)-LSSTE-
VGSNT-Hyp-$NH_2$ (Compound 7)
(SEQ ID NO: 61)
[19CD]-isoGlu-RD()GTAT-Orn()-ATERLAHFLHRSSF-
Gly(Me)-A-Ile(Me)-LSSTEVGSNTP-$NH_2$ -continued (Compound 8)
(SEQ ID NO: 62)
[19CD]-isoGlu-RD()GTAT-Orn()-ATQRLAHFLQRSSF-Gly(Me)-A-Ile(Me)-LSSTEVGSNT-Hyp-NH$_2$ (Compound 9)
(SEQ ID NO: 63)
[19CD]-isoGlu-RD()GTAT-Orn()-ATQRLAHFLQRSSF-Gly(Me)-A-Ile(Me)-PSSTEVGSNT-Hyp-NH$_2$ (Compound 10)
(SEQ ID NO: 64)
[19CD]-isoGlu-RD()GTAT-Orn()-ATERLARFLQRSSF-Gly(Me)-A-Ile(Me)-LSSTEVGSNT-Hyp-NH$_2$ (Compound 11)
(SEQ ID NO: 65)
[19CD]-isoGlu-ED()GTATK()ATERLAHFLQRSSF-Gly(Me)-A-Ile(Me)-LSSTE-VGSNT-Hyp-NH$_2$ (Compound 12)
(SEQ ID NO: 66)
[19CD]-isoGlu-RD()GEATK()ATERLAHFLQRSSF-Gly(Me)-A-Ile(Me)-LSSTE-VGSNT-Hyp-NH$_2$ (Compound 13)
(SEQ ID NO: 67)
[19CD]-isoGlu-RD()GTLTK()ATERLAHFLQRSSF-Gly(Me)-A-Ile(Me)-LSSTE-VGSNT-Hyp-NH$_2$ (Compound 14)
(SEQ ID NO: 68)
[19CD]-isoGlu-RD()GTASK()ATERLAHFLQRSSF-Gly(Me)-A-Ile(Me)-LSSTE-VGSNT-Hyp-NH$_2$ (Compound 15)
(SEQ ID NO: 69)
[19CD]-isoGlu-RD()GTATK()ATQRLAHFLQRSSF-Gly(Me)-A-Ile(Me)-PSSTE-VGSNT-Hyp-NH$_2$ (Compound 16)
(SEQ ID NO: 70)
[19CD]-isoGlu-RD()GTATK()ATQRLAHFLQRSSF-Gly(Me)-A-Ile(Me)-LSSTE-VGSNT-Hyp-NH$_2$ (Compound 17)
(SEQ ID NO: 71)
[19CD]-isoGlu-RD()GTATK()ATERLAHFLQRSSF-Gly(Me)-A-Ile(Me)-PSSTE-VGSNT-Hyp-NH$_2$ (Compound 18)
(SEQ ID NO: 72)
[19CD]-isoGlu-RD()GTATK()ATERLAHFLQRSSF-Gly(Me)-A-Ile(Me)-LSSTE-VGSNT-Hyp-NH$_2$ (Compound 19)
(SEQ ID NO: 73)
[19CD]-isoGlu-RD()GTAT-hLys()-ATERLAHFLQRSSF-Gly(Me)-A-Ile(Me)-LSSTEVGSNT-Hyp-NH$_2$ (Compound 20)
(SEQ ID NO: 74)
[19CD]-isoGlu-RD()GTAT-Orn()-ATERLA-Aad-FLQRSSF-Gly(Me)-A-Ile(Me)-LSSTEVGSNT-Hyp-NH$_2$ (Compound 21)
(SEQ ID NO: 75)
[19CD]-isoGlu-RD()GTAT-Orn()-ATERLA-Aad-FLQRSSF-Gly(Me)-A-Ile(Me)-PSSTEVGSNT-Hyp-NH$_2$ (Compound 22)
(SEQ ID NO: 76)
[19CD]-isoGlu-RD()GTAT-Orn()-ATERLA-Aad-FLTRSSF-Gly(Me)-A-Ile(Me)-LSSTEVGSST-Hyp-NH$_2$ (Compound 23)
(SEQ ID NO: 77)
[19CD]-isoGlu-RD()GTAT-Orn()-ATERLA-Aad-FLQRTTF-Gly(Me)-A-Ile(Me)-LSSTEVGSNT-Hyp-NH$_2$ (Compound 24)
(SEQ ID NO: 78)
[19CD]-isoGlu-RD()GTAT-Orn()-ATERLA-Aad-FLQRTTF-Gly(Me)-A-Ile(Me)-PSSTEVGSNT-Hyp-NH$_2$ (Compound 25)
(SEQ ID NO: 79)
[19CD]-isoGlu-RD()GTAT-Orn()-ATERLA-Aad-FLQRATF-Gly(Me)-A-Ile(Me)-LSSTEVGSNT-Hyp-NH$_2$ (Compound 26)
(SEQ ID NO: 80)
[19CD]-isoGlu-RD()GTAT-Orn()-ATERLA-Aad-FLQRAAF-Gly(Me)-A-Ile(Me)-LSSTEVGSNT-Hyp-NH$_2$ (Compound 27)
(SEQ ID NO: 81)
[19CD]-isoGlu-RD()GTAT-Orn()-ATERLA-Aad-FLQRGTF-Gly(Me)-A-Ile(Me)-LSSTEVGSNT-Hyp-NH$_2$ (Compound 28)
(SEQ ID NO: 82)
[19CD]-isoGlu-RD()QTAT-Orn()-ATERLA-Aad-FLQRGTF-Gly(Me)-A-Ile(Me)-LSSTEVGSNT-Hyp-NH$_2$ (Compound 29)
(SEQ ID NO: 83)
[19CD]-isoGlu-RD()PTATK()ATERLA-Aad-FLQRSSF-Gly(Me)-A-Ile(Me)-LSSTEVGSNT-Hyp-NH$_2$ (Compound 30)
(SEQ ID NO: 84)
[19CD]-isoGlu-ED()GTATK()ATERLA-Aad-FLQRSSF-Gly(Me)-A-Ile(Me)-PSSTEVGSNT-Hyp-NH$_2$ (Compound 31)
(SEQ ID NO: 85)
[19CD]-isoGlu-RD()GTATK()ATERLA-Aad-FLQRAAF-Gly(Me)-A-Ile(Me)-LSSTEVGSNT-Hyp-NH$_2$ (Compound 32)
(SEQ ID NO: 86)
[19CD]-isoGlu-RD()GTATK()ATERLA-Aad-FLQRGGF-Gly(Me)-A-Ile(Me)-LSSTEVGSNT-Hyp-NH$_2$ (Compound 33)
(SEQ ID NO: 87)
[19CD]-isoGlu-RD()GTATK()ATERLA-Aad-FLQRANF-Gly(Me)-A-Ile(Me)-LSSTEVGSNT-Hyp-NH$_2$ -continued (Compound 34)
(SEQ ID NO: 88)
[19CD]-isoGlu-RD()GTATK()ATERLA-Aad-FLQRSSF-Gly(Me)-A-Ile(Me)-PSSTEVGSNT-Hyp-NH$_2$ (Compound 35)
(SEQ ID NO: 89)
[19CD]-isoGlu-RD()GTATK()ATERLA-Aad-FLQRSSF-Gly(Me)-A-Ile(Me)-LSSTEVGSNT-Hyp-NH$_2$ (Compound 36)
(SEQ ID NO: 90)
[19CD]-isoGlu-RD()GTATK()ATERLA-Aad-FLQRSSF-Gly(Me)-A-Ile(Me)-LSSTETGSNT-Hyp-NH$_2$ (Compound 37)
(SEQ ID NO: 91)
[19CD]-isoGlu-ED()GTATK()ATERLA-Aad-FLQRSSF-Gly(Me)-A-Ile(Me)-LSSTEVGSNT-Hyp-NH$_2$ (Compound 38)
(SEQ ID NO: 92)
[19CD]-isoGlu-RD()GTATK()ATERLA-Aad-FLQRTTF-Gly(Me)-A-Ile(Me)-LSSTEVGSNT-Hyp-NH$_2$ (Compound 39)
(SEQ ID NO: 93)
[19CD]-isoGlu-KD()GTATK()ATQRLA-Aad-FLQRSSF-Gly(Me)-AIle(Me)-LSSTEVGSNTHyp-NH$_2$ (Compound 40)
(SEQ ID NO: 94)
[19CD]-isoGlu-RD()GTATK()ATQRLA-Aad-FLQRSSF-Gly(Me)-A-Ile(Me)-LSSTEVGSNT-Hyp-NH$_2$ (Compound 41)
(SEQ ID NO: 95)
[19CD]-isoGlu-RD()GTATK()ATQRLADFLQRSSF-Gly(Me)-A-Ile(Me)-LSSTE-VGSNT-Hyp-NH$_2$ (Compound 42)
(SEQ ID NO: 96)
[19CD]-isoGlu-RD()GTATK()ATQRLADFLQRSSF-Gly(Me)-A-Ile(Me)-LSSTETGSNT-Hyp-NH$_2$ (Compound 43)
(SEQ ID NO: 97)
[19CD]-isoGlu-KD()GTATK()ATQRLANFLQRSSF-Gly(Me)-A-Ile(Me)-LSSTE-VGSNT-Hyp-NH$_2$ (Compound 44)
(SEQ ID NO: 98)
[19CD]-isoGiu-KD()GTATK()ATQRLANFLQRSSF-Gly(Me)-A-Ile(Me)-LSSTETGSNT-Hyp-NH$_2$ (Compound 45)
(SEQ ID NO: 99)
[19CD]-isoGlu-R-Dap()-GTATD()ATERLAHFLQRSSF-Gly(Me)-A-Ile(Me)-LSSTEVGSNT-Hyp-NH$_2$ (Compound 46)
(SEQ ID NO: 100)
[19CD]-isoGlu-R-Dab()-GTATD()ATERLAHFLQRSSF-Gly(Me)-A-Ile(Me)-LSSTEVGSNT-Hyp-NH$_2$ (Compound 47)
(SEQ ID NO: 101)
[19CD]-isoGlu-R-Orn()-GTATD()ATERLAHFLQRSSF-Gly(Me)-A-Ile(Me)-LSSTEVGSNT-Hyp-NH$_2$ (Compound 48)
(SEQ ID NO: 102)
[19CD]-isoGlu-R-Dap()-GTAT-Aad()-ATERLAHFLQRSSF-Gly(Me)-A-Ile(Me)-LSSTEVGSNT-Hyp-NH$_2$ (Compound 49)
(SEQ ID NO: 103)
[19CD]-isoGlu-R-Dab()-GTATE()ATERLAHFLQRSSF-Gly(Me)-A-Ile(Me)-LSSTEVGSNT-Hyp-NH$_2$ (Compound 50)
(SEQ ID NO: 104)
[19CD]-isoGlu-R-Aad()-GTAT-Dap()-ATERLAHFLQRSSF-Gly(Me)-A-Ile(Me)-LSSTEVGSNT-Hyp-NH$_2$ (Compound 51)
(SEQ ID NO: 105)
[19CD]-isoGlu-RE()GTAT-Dab()-ATERLAHFLQRSSF-Gly(Me)-A-Ile(Me)-LSSTEVGSNT-Hyp-NH$_2$ For comparison purposes, three compounds having disulphide bridges (instead of lactam bridges) and two uncyclised compounds were synthesised:

Ref.1
(SEQ ID NO: 106)
[19CD]-isoGlu-RDGTAT-Orn-ATERLAHFLQRSSF-Sar-A-Ile(Me)-PSSTEVGSNT-Hyp-NH$_2$ Ref.2
(SEQ ID NO: 107)
[19CD]-isoGlu-RC()GTATC()ATERLAHFLQRSSF-Sar-A-Ile(Me)-LSSTEVGSNT-Hyp-NH$_2$ Ref.3
(SEQ ID NO: 108)
[19CD]-isoGlu-RDGTAT-Orn-ATERLA-Aad-FLQRSSF-Sar-A-Ile(Me)-LSSTE-VGSNT-Hyp-NH$_2$ Ref.4
(SEQ ID NO: 109)
[19CD]-isoGlu-RC()GTATC()ATERLA-Aad-FLQRSSF-Sar-A-Ile(Me)-LSSTE-VGSNT-Hyp-NH$_2$ Ref.5
(SEQ ID NO: 110)
[19CD]-isoGlu-RC()NTATC()ATQRLADFLQRSSF-Sar-A-Ile(Me)-LSSTEVGSNT-Hyp-NH$_2$ A further reference compound, designated NN96, is {N-α-[(S)-4-carboxy-4-(19-carboxynonadecanoylamino)butyryl]-[Arg1, Glu14, His17, Pro37]-pramlintide; disclosed as Example 96 in WO 2012/168430 A2, and having the amino acid sequence RC( )NTATC( )ATQRLAE-FLHHSSNNFGPILPPTNVGSNTP.

Parentheses "( )" indicate intramolecular lactam bridges (or disulphide bridges, where appropriate) formed between the side chains of the residues at positions 2 and 7 of the relevant amino acid sequences.

Unless otherwise specified, reagents and solvents employed in the following were available commercially in standard laboratory reagent or analytical grade, and were used without further purification.

General procedures for solid-phase synthesis of peptides

A CEM Liberty Peptide Synthesizer or a CEM Liberty Blue Peptide Synthesizer was employed, using standard Fmoc chemistry. TentaGel™ S Ram resin (1 g; 0.25 mmol/g) was swelled in DMF (10 ml) prior to use and transferred between tube and reaction vessel using DCM and DMF. Pseudoprolines [i.e. dipeptides employed to minimize aggregation during peptide synthesis, such as Fmoc-Phe-Thr(ψ-Me, Me-Pro)-OH and Fmoc-Asp-Ser(ψ-Me, Me-Pro)-OH and Fmoc-Ser-Ser(ψ-Me, Me-Pro)-OH] were used where appropriate, and non-naturally occurring amino acids and other suitable building blocks were employed without any changes to the general procedure.

The following optical isomers of particular amino acids (including non-naturally occurring amino acids) were employed in the synthesis of the compounds:

Hyp: (2S,4R)-4-hydroxyproline [also denoted (4R)-4-hydroxy-L-proline].

Aad: (2S)-2-aminoadipic acid

Dab: (2S)-2,4-diaminobutanoic acid

Dap: (2S)-2,3-diaminopropanoic acid hLys: (2S)-2-amino-7-amino-heptanoic acid, also known as homo-lysine Gly(Me): N-methylglycine, also known as sarcosine Ile(Me): N-methylisoleucine Coupling CEM Liberty Peptide Synthesizer: an Fmoc-amino acid in DMF/DCM (2:1; 0.2 M; 5 mL) was added to the resin in a CEM Discover microwave unit together with COMU/DMF (0.5 M; 2 mL) and DIPEA/NMP (2.0 M; 1 mL). The coupling mixture was heated to 75° C. for 5 min while nitrogen was bubbled through the mixture. The resin was then washed with DMF (4×10 mL). Alternatively the coupling was done without heating and the reaction time extended to 60 min in this case.

CEM Liberty Blue Peptide Synthesizer: an Fmoc-amino acid in DMF (0.2 M; 5 mL) was added to the resin in a CEM Discover microwave unit together with DIC/DMF (0.5 M; 2 mL) and Oxyma/DMF (2.0 M; 1 mL). The coupling mixture was heated to 90° C. for 2 min while nitrogen was bubbled through the mixture. The resin was then washed with DMF (4×10 mL). Alternatively the coupling was done without heating and the reaction time extended to 60 min in this case.

Independent of CEM Synthesizer type, in the case of difficult couplings (e.g. coupling of a residue immediately after an N-methylated amino acid residue or other sterically hindered amino acid residue as recognized by a person of skill in the art) the coupling was repeated one or more times.

Deprotection

Piperidine/DMF (1:4, i.e. 1 part piperidine to 4 parts DMF by volume; 10 mL) was added to the resin for initial deprotection, and the mixture was microwave-heated (40° C.; 30 sec). The reaction vessel was drained and a second portion of piperidine/DMF (1:4; 10 mL) was added and heated (75° C.; 3 min) again. The resin was then washed with DMF (6×10 mL).

Oxidative Cyclisation

Intramolecular ring formation (disulfide bridge formation) between Cys residues in positions 2 and 7 (initially coupled in the form of Acm-protected cysteines) was performed with the peptide still attached to the resin, using 163 mg thallium(III) trifluoroacetate [Tl(TFA)$_3$] in 5 mL NMP in a simultaneous Acm-deprotection and disulfide-formation step. (alternative method: addition of 10 eq of iodine to a 50 mM solution of resin bound peptide in acetic acid and stirring for 18-24 h)

Lactam Cyclisation

The following procedure for the coupling of Asp and Lys is representative for all lactam formations where the amino acid side chain containing the carboxyl-function is protected with OAll and the amino acid side chain containing the amino group is Alloc-protected. After assembly of the full peptide sequence, deprotection of Asp(OAll) in position 2 and Lys(Alloc) in position 7 was performed using 29 mg tetrakis(triphenylphosphine)palladium(0) and phenylsilane 125 µL in 20 mL DCM. Subsequently, the lactam bridge was formed between the Asp residue (2) and Lys residue (7) using 414 mg HCTU and 346 µL DIPEA in 20 mL DMF. Both steps were performed with the peptide still attached to the resin.

Cleavage

The resin was washed with EtOH (3×10 mL) and Et$_2$O (3×10 mL) and dried to constant weight at room temperature (r.t.). The crude peptide was cleaved from the resin by treatment with TFA/TIS/H$_2$O (90:5:5; 40 mL; 2 h; r.t.) or alternatively with TFA/DODT (95:5; 40 mL; 2 h; r.t.). Most of the TFA was removed under reduced pressure, and the crude peptide was precipitated and washed three times with Et$_2$O and dried to constant weight at room temperature.

Purification and Characterisation

The crude peptide was purified by preparative reverse phase HPLC using a gradient of solvent A (0.1% aqueous TFA) and solvent B (0.1% TFA, 90% MeCN in water) on either a PerSeptive Biosystems VISION Workstation or a Gilson system (Pumps: "Pump 305", "331 Pump", "332 Pump", "402 Syringe Pump"; column changer "Valvemate® II" UV detector "UV/Vis-155"; and the fraction collector "GX 281" equipped with a suitable column and a fraction collector) or a Waters Autopurification HPLC/MS System (2525 pump System, Waters 2996 DAD, sample manager Waters 2767, MS ZQ single quadrupole. Columns: XSelect CSH 130 Prep C18 5 mm ODB 30×150 mm or Kinetex 5 mm C8 100A 150×21,2 mm). Fractions were analysed by analytical HPLC and MS, and relevant fractions were pooled and lyophilised. The final product was characterized by HPLC and MS.

One of skill in the art will appreciate that standard methods of peptide synthesis may be used to generate the compounds of the invention.

Example 2 hCT-R and hAMYR3 Assays

For the assessment of the in vitro activity of test peptides, cell lines expressing recombinant human calcitonin receptor (hCT-R) or recombinant human amylin 3 receptor (hAMYR3) in the background of the human astrocytoma cell line 1321N1 were purchased from DiscoveRx Corporation (Cat. No. 95-016106 and 95-0166C6). The hAMYR3 is a hetero-oligomer of the calcitonin receptor (Isoform 2; Gene ID 799) and RAMPS (Gene ID 10268) that forms when both genes are expressed in the same cell. The hCT-R cell line expresses only the recombinant human calcitonin receptor gene (Isoform 2; Gene ID 799). Upon activation of hCT-R or hAMYR3 by the test peptides the formation of cAMP is induced and was measured using the AlphaScreen® cAMP Assay kit from Perkin-Elmer (Cat. No. 6760635R).

Briefly, 1321N1 cells expressing hCT-R or hAMYR3 were seeded in 384-well microtiter plates (Falcon Optilux White, Cat.-No. 10448642) at 5,000 cells in 50 μL growth medium per well (AssayComplete 1321N1 Cell Culture Kit, DiscoveRx Corp.), and incubated for 24 h at 37° C., 5% $CO_2$. On the day of analysis growth medium was removed and the cells were stimulated by adding 10 μL of stimulation buffer (10 nM Hepes pH 7.4, 140 nM NaCl, 3.6 nM KCl, 0.5 nM $NaH_2PO_4$, 0.5 nM $MgSO_4$, 1.5 nM $CaCl_2$, 5 nM $NaHCO_3$, 0.5 nM IBMX, 0.1% BSA) containing increasing concentrations of test peptides, and incubation for 45 min at room temperature. The stimulation was stopped by adding 5.6 μL/well donor bead detection mix (5 mM Hepes pH7.4, 0.5% TWEEN 20, 0.1% BSA, 0.05 mg/mL donor beads, 62.5 nM biotinylated cAMP) and 4.5 μL/well acceptor bead solution (5 mM Hepes pH7.4, 0.5% TWEEN 20, 0.1% BSA, 0.05 mg/mL acceptor beads). After thorough mixing the plates were incubated in the dark for 1 h at room temperature and the cAMP content of the resulting cell lysates was estimated according to the AlphaScreen® cAMP Assay manufacturer's instructions. EC50 values were estimated by computer-aided curve fitting of results of at least 7 different compound concentrations.

The in vitro activity results (expressed as $EC_{50}$ values) are summarized in Table 1, below.

Example 3

Solubility Determination

Test peptide is weighed into a suitable vial and the respective buffer (acetate buffer pH 4.0, phosphate buffer pH 6, histidine buffer pH 6 and 7; all at 40 nM concentration) added to a total volume of 0.5 mL.

Vials are shaken at room temperature for 2 h and filtered through a 0.45 μm filter. The resulting solutions are analyzed by RP-HPLC on a C18 column with gradient elution using a formic acid/acetonitrile/water eluent system. The area of the main peak is determined by UV spectroscopy at 230 nm at each sampling time point. The dissolved concentration is calculated by an external standard method.

Example 4

Assessment of Physical Stability

Aggregation in the form of fibril formation was detected using the amyloid-specific dye Thioflavin T (ThT), which is frequently employed to demonstrate the presence of fibrils in solution (see, e.g., Groenning, M., J. Chem. Biol. 3(1) (2010), pp. 1-18; Groenning et al., J. Struct. Biol. 158 (2007) pp. 358-369; and Levine, H., III, Protein Sci. 2 (1993) pp. 404-410) Test peptides (2 mg/mL) were dissolved in demineralized water adjusted to pH 2.5 with HCl, at ambient temperature (typically 25° C.). Solutions containing (i) 1 mg/mL of test peptide, 40 μM ThT and 50 mM phosphate (Ph) buffer (pH 7.0), (ii) 1 mg/mL of test peptide, 40 μM ThT and 50 mM histidine (His) buffer (pH 7.0), and (iii) 1 mg/mL of test peptide, 40 μM ThT and 50 mM acetate (Ac) buffer (pH 4.0), were loaded in a 96-well black fluorescence plate (clear bottom) in triplicate. Data were collected at fixed intervals of 10 min, each preceded by 300 s of automixing (agitation), over a period of 96 hours at 40° C. Physical stability is determined by measuring the fluorescence intensity over time. A significant increase in intensity is rated as fibrillation detected (FD). Data are summarized in Table 1 below.

Example 5

Assessment of Chemical Stability

Samples of each test peptide were dissolved in acetate buffer pH 4 and phosphate buffer pH 6 and 7 (all buffer 40 mM). The final peptide concentration was 1 mg/mL. Samples were placed in glass vials and incubated at 40° C. The samples were analyzed by RP-HPLC on a C8 column with gradient elution using a trifluoroacetic acid/acetonitrile/water eluent system. The area-percentage (area-%) of the main peak was determined by UV spectroscopy at 220 nm at each sampling time point.

The % degradation was calculated by subtracting the main peak area percentage at start (t=0) from the main peak area percentage at each sampling time point.

The results of the chemical stability assessment after 3 days of incubation time are summarized as % degradation in Table 1 (below).

The results of the chemical stability assessment after 14 days of incubation time are summarized as % degradation in Table 2 (below).

In an alternative analysis, peptides were dissolved in MilliQ water and pH adjusted to 4.0, 7.5 or 9.0. Samples were placed in glass vials and incubated at 40° C. The samples were analyzed by RP-HPLC on a C8 column with gradient elution using a trifluoroacetic acid/acetonitrile/water eluent system. The area-percentage (area-%) of the main peak was determined by UV spectroscopy at 220 nm at each sampling time point.

The % degradation was calculated by subtracting the main peak area percentage at start (t=0) from the main peak area percentage at each sampling time point.

The results of the chemical stability assessment after 8 days of incubation time are summarized as % degradation in Table 3 (below).

TABLE 1

| | | | | | | % degradation after 72 h at 40° C. | | |
|---|---|---|---|---|---|---|---|---|
| | hCT-R | hAMYR3 | Fibrillation* (in buffer) | | | | | |
| Compound no. | EC50 [nM] | EC50 [nM] | pH4 acetate | pH7 histidine | pH7 phosphate | pH4 acetate | pH6 phosphate | pH7 phosphate |
| 1 | 13.6 | 9.3 | | | | | | |
| 2 | 0.105 | 0.032 | | | | | | |
| 3 | 0.081 | 0.035 | FND | FND | FD | <1 | 3.2 | 1.2 |
| 4 | 0.160 | 0.092 | FND | FND | FND | <1 | <1 | <1 |
| 5 | 0.114 | 0.032 | | | | | | |
| 6 | 0.327 | 0.011 | | | | | | |
| 7 | 0.289 | 0.032 | | | | | | |
| 8 | 0.129 | 0.059 | FND | FND | FND | <1 | <1 | <1 |
| 9 | 0.027 | 0.013 | | | | | | |
| 10 | 0.345 | 0.068 | FD | FND | FND | <1 | <1 | <1 |
| 11 | 0.068 | 0.024 | FND | FND | FND | <1 | <1 | <1 |
| 12 | 0.893 | 0.999 | | | | | | |
| 13 | 1.411 | 0.456 | | | | | | |
| 14 | 0.386 | 0.108 | | | | | | |
| 15 | 0.056 | 0.017 | FND | FD | FD | <1 | <1 | <1 |
| 16 | 0.043 | 0.035 | | | | | | |
| 17 | 0.058 | 0.025 | FND | FND | FND | 1.2 | <1 | <1 |
| 18 | 0.085 | 0.031 | FND | FND | FND | <1 | <1 | <1 |
| 19 | 0.028 | 0.006 | | | | | | |
| 20 | 0.009 | 0.003 | FD | FND | FND | 1.0 | 1.3 | 2.0 |
| 21 | 0.037 | 0.010 | FND | FND | FND | <1 | <1 | <1 |
| 22 | 0.474 | 0.051 | | | | | | |
| 23 | 1.931 | 0.706 | | | | | | |
| 24 | 0.038 | 0.013 | | | | | | |
| 25 | 0.844 | 0.336 | FND | FND | FND | — | — | <1 |
| 26 | 0.769 | 0.120 | | | | | | |
| 27 | 0.521 | 0.325 | FND | FND | FND | <1 | <1 | 1.7 |
| 28 | 1.229 | 0.268 | | | | | | |
| 29 | 1.070 | 0.312 | | | | | | |
| 30 | 0.232 | 0.122 | FD | FND | FND | | | |
| 31 | 0.227 | 0.066 | | | | | | |
| 32 | 0.006 | 0.005 | FD | FND | FND | 1.3 | <1 | 2.2 |
| 33 | 0.019 | 0.009 | FND | FND | FND | <1 | 1 | <1 |
| 34 | 0.206 | 0.063 | FND | FND | FND | <1 | <1 | 2.8 |
| 35 | 0.066 | 0.028 | FND | FND | FND | <1 | <1 | 1.4 |
| 36 | 0.026 | 0.007 | FD | FND | FND | 2.5 | 2.1 | 1.0 |
| 37 | 0.116 | 0.031 | FD | FND | FND | — | <1 | 3.0 |
| 38 | 0.114 | 0.060 | FD | FND | FND | <1 | <1 | <1 |
| 39 | 0.094 | 0.024 | FD | FND | FND | <1 | <1 | <1 |
| 40 | 0.028 | 0.008 | FD | FND | FND | 1.1 | <1 | <1 |
| 41 | 0.095 | 0.024 | FND | FND | FND | <1 | <1 | <1 |
| 42 | 0.006 | 0.003 | | | | | | |
| 43 | 0.021 | 0.007 | FD | FD | FD | | | |
| 44 | 0.020 | 0.009 | FD | FND | FND | | | |
| 45 | 299 | 279 | | | | | | |
| 46 | 7.5 | 5.5 | | | | | | |
| 47 | 10.8 | 7.7 | | | | | | |
| 48 | 0.107 | 0.020 | | | | | | |
| 49 | 1.038 | 0.442 | | | | | | |
| 50 | 3.3 | 1.5 | | | | | | |
| 51 | 0.861 | 0.306 | | | | | | |
| Ref. 1 | 20.3 | 17.1 | | | | | | |
| Ref. 2 | 0.019 | 0.003 | | | | | | |
| Ref. 3 | 18.2 | 13.2 | | | | | | |
| Ref. 4 | 0.075 | 0.031 | FND | FND | FND | | | |
| Ref. 5 | 0.063 | 0.028 | FD | FND | FND | | | |

*FND = fibrillation not detected;
FD = fibrillation detected

TABLE 2

Chemical stability

| Compound no. | % degradation after 14 days at 40° C. | | |
|---|---|---|---|
| | pH 4 acetate | pH 6 phosphate | pH 7 phosphate |
| 32 | <1 | <1 | <1 |
| 41 | 1.1 | <1 | <1 |
| 10 | 1.9 | 1.8 | 9.1 |
| 14 | 2.2 | <1 | 2.6 |
| 18 | <1 | 1.0 | 1.9 |
| 37 | ND | <1 | <1 |
| 36 | ND | 1.6 | <1 |
| 4 | 1.6 | <1 | 6.4 |
| 38 | ND | ND | <1 |
| 20 | ND | <1 | 3.7 |
| 16 | ND | <1 | ND |
| 3 | ND | 1.0 | ND |
| 35 | 2 | <1 | <1 |
| Ref. 2 | <1 | 4.6 | ND |
| Ref. 4 | 3.2 | 12.6 | 20.3 |
| Ref. 5 | 3.0 | 5.1 | 12.7 |
| NN96 | 3.0 | 10.1 | 33.2 |

ND—not determined

TABLE 3

Chemical stability

| Compound no. | % degradation after 8 days at 40° C. | | |
|---|---|---|---|
| | pH 4 | pH 7.5 | pH 9 |
| 51 | 3.1 | 4.6 | 4.6 |
| 49 | 1.7 | 2.1 | 3.0 |
| 48 | 1.8 | 2.3 | 2.5 |
| 19 | 3.9 | 6.2 | 4.2 |

Example 6

Pharmacokinetic (PK) Profiling in Rats

Sprague Dawley male rats were given a single subcutaneous (sc) bolus of each peptide to be tested, as specified below.

30 nmol/kg doses of compound were administered. Blood samples were drawn from the tail vein prior to dosing and at 24 and 96 hours after dosing. The rats were euthanized immediately after the last blood sampling by concussion and cervical dislocation.

The dosing vehicle used for each test peptide was a mannitol-containing histidine buffer (pH 7.0). Plasma samples were analyzed after precipitation with ethanol by liquid chromatography mass spectrometry (LC-MS/MS). Mean plasma concentrations were used for calculation of the pharmacokinetic parameters.

Plasma terminal elimination half-life ($t_{1/2}$) was determined as $\ln(2)/\lambda z$, where $\lambda z$ is the magnitude of the slope of the log linear regression of the log concentration versus time profile during the terminal phase.

Results

The plasma terminal elimination half-lives ($t_{1/2}$) for all tested peptides were determined to be in the range of 21.3 h to 36.1 h.

TABLE 4 in vivo half life

| Compound No. | $t_{1/2}$ [h] |
|---|---|
| 3 | 21.3 |
| 4 | 31.9 |
| 18 | 30.1 |
| 20 | 31.1 |
| 35 | 36.1 |
| 38 | 31.8 |

Example 7

Effect on Acute Food Intake and Body Weight in Normal Sprague Dawley Rats

Sprague Dawley (SD) rats were obtained from Janvier Labs, France. The animals arrived at least 14 days before the study start to allow acclimatization to experimental conditions. From arrival and throughout the study, the rats were housed in groups of 2 to 4 (n=2-4) in a light-, temperature- and humidity-controlled room. Animals had access ad libitum to food (KLIBA 3430, Provimi Kliba AG, Switzerland) and water (domestic quality tap water) during the entire study. Per group 6-8 rats were included. A vehicle group and positive control group were included in each set of tests. Rats were dosed subcutaneously (sc) once in the morning 1 hour before turning off the lights, using a body weight-corrected dose (30 nmol/kg) of test peptide. Dosing volume was 2 ml/kg. Food intake was recorded online using an automated food intake system (HM02, MBRose, Denmark) for 4 days or manually at 0 h for a predose and then 24, 48, 72 and 96 h post dosing. Body weight was measured daily.

Statistical analyses were performed using GraphPad™ Prism version 7. The measured parameters were compared using two-way ANOVA followed by Dunnett's multiple comparison tests. Differences were considered statistically significant at $p<0.05$.

Results 48 h after dosing, each of the tested compounds (except for compounds 30 and 37) had given rise to a clear, statistically significant inhibition of food intake (vehicle-corrected, in %). This reduction in food intake was reflected by a decrease in body weight (vehicle-corrected, in %). Normal feeding behavior was subsequently resumed.

TABLE 5

Effect on food intake and body weight

| Compound No. | Food intake reduction in % at 48 h Dose: 30 nmol/kg | Body weight reduction in % at 48 h Dose: 30 nmol/kg |
|---|---|---|
| 41 | 75 | 11 |
| 35 | 72 | 12 |
| 18 | 58 | 10 |
| 39 | 76 | 9.2 |
| 40 | 83 | 7.3 |
| 37 | 24 | 4.3 |
| 30 | <20 | 0 |
| 36 | 44 (at dose of 10 nmol/kg) | 5.2 (at dose of 10 nmol/kg) |
| 4 | 34 | 4.6 |
| 38 | 43 | 8.2 |
| 20 | 49 | 7.8 |

TABLE 5-continued

Effect on food intake and body weight

| Compound No. | Food intake reduction in % at 48 h Dose: 30 nmol/kg | Body weight reduction in % at 48 h Dose: 30 nmol/kg |
|---|---|---|
| 15 | 71 | 7.7 |
| 16 | 66 | 7.4 |
| 3 | 34 | 5.6 |

Example 8

Acute Fed Basal Glucose Changes in Diabetic ZDF Rats

Male Zucker Diabetic Fatty rat (ZDF-Lepr$^{fa}$/Crl) are obtained from Charles River, US. Animals are acclimatised to experimental conditions for at least 14 days before the start of the study. From arrival and throughout the study, the rats are housed in groups of 2 (n=2) in a light-, temperature- and humidity-controlled room. Animals have access ad libitum to food (KLIBA 2437, Provimi Kliba AG, Switzerland) and water (domestic quality tap water) during the entire study.

Rats are randomized based on blood glucose, HbA1c and body weight into a designated test and vehicle group. The total number of animals per group is 10 (n=10). Rats are dosed subcutaneously (sc) once in the morning using a body weight-corrected dose (10 nmol/kg) of test peptide. Dosing volume is 2 ml/kg.

Blood glucose levels in tail blood samples taken 24, 72, 96 and 168 hours post dosing and blood glucose levels are determined using a glucometer (GlucoSmart Swing™; MSP Bodmann GmbH, Germany).

Statistical analyses are performed using GraphPad™ Prism version 7. The measured parameters are compared using two-way ANOVA followed by Sidak multiple comparison tests. Differences are considered statistically significant at $p<0.05$.

The invention claimed is:

1. An amylin analogue which is a compound having the formula:

(SEQ ID NO: 89)
[19CD]-isoGlu-RD()GTATK()ATERLA-Aad-

FLQRSSF-Gly(Me)-A-Ile(Me)-LSSTEVGSNT-

Hyp-NH$_2$ wherein an intramolecular lactam bridge is formed between the side chains of residues indicated by parentheses "( )"; and wherein [19CD]-isoGlu is a 19-carboxynonadecanoyl group covalently attached to the alpha amino group of an iso-glutamic acid linker;
or a pharmaceutically acceptable salt thereof.

2. A method of treating obesity, inhibiting weight gain, promoting weight loss, reducing food intake, and/or reducing excess body weight in a subject in need thereof, comprising administering to the subject an effective amount of an amylin analogue according to claim 1.

3. The method of claim 2, wherein the method comprises inhibiting weight gain, promoting weight loss, and/or reducing excess body weight in a subject in need thereof by administering to the subject an effective amount of the amylin analogue.

4. The method of claim 2, wherein the method comprises treating obesity in a subject in need thereof by administering to the subject an effective amount of the amylin analogue.

5. The method of claim 2, wherein the method comprises reducing food intake in a subject in need thereof by administering to the subject an effective amount of the amylin analogue.

6. The method of claim 2, wherein the subject is suffering from diabetes.

7. The method of claim 2, wherein the subject is suffering from hypertension.

8. The method of claim 2, wherein the subject is suffering from dyslipidemia.

9. The method of claim 2, wherein the subject is suffering from sleep apnea.

10. The method of claim 2, wherein the subject is suffering from cardiovascular disease.

11. The method of claim 2, wherein the amylin analogue is administered subcutaneously.

12. The method of claim 11, wherein administration occurs once weekly.

13. A method of treating osteoarthritis, Prader-Willi syndrome, sleep apnea, Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis, non-alcoholic fatty liver disease (NAFLD), non-alcoholic steatohepatitis (NASH), kidney failure, arteriosclerosis, (e.g. atherosclerosis), macrovascular disease, microvascular disease, diabetic heart disease, diabetic cardiomyopathy, heart failure as a diabetic complication, coronary heart disease, peripheral artery disease or stroke, and combinations thereof, in a subject in need thereof, comprising administering to the subject an effective amount of an amylin analogue according to claim 1.

14. The method of claim 13, wherein the method comprises treating osteoarthritis in a subject in need thereof by administering to the subject an effective amount of the amylin analogue.

15. The method of claim 13, wherein the method comprises treating type 1 diabetes in a subject in need thereof by administering to the subject an effective amount of the amylin analogue.

16. The method of claim 13, wherein the method comprises treating type 2 diabetes in a subject in need thereof by administering to the subject an effective amount of the amylin analogue.

17. The method of claim 13, wherein the method comprises treating NASH in a subject in need thereof by administering to the subject an effective amount of the amylin analogue.

18. The method of claim 13, wherein the method comprises treating Prader-Willi syndrome in a subject in need thereof by administering to the subject an effective amount of the amylin analogue.

19. The method of claim 13, wherein the method comprises treating sleep apnea in a subject in need thereof by administering to the subject an effective amount of the amylin analogue.

20. The method of claim 13, wherein the method comprises treating diabetic heart disease in a subject in need thereof by administering to the subject an effective amount of the amylin analogue.

21. The method of claim 20, wherein the method comprises treating diabetic cardiomyopathy in a subject in need thereof by administering to the subject an effective amount of the amylin analogue.

22. The method of claim 20, wherein the method comprises treating heart failure as a diabetic complication in a subject in need thereof by administering to the subject an effective amount of the amylin analogue.

23. The method of claim 13, wherein the amylin analogue is administered subcutaneously.

24. The method of claim 23, wherein administration occurs once weekly.

25. A method of lowering circulating LDL levels and/or increasing HDL/LDL ratio in a subject in need thereof, comprising administering to the subject an effective amount of an amylin analogue according to claim 1.

26. The method of claim 25, wherein the subject is obese.

27. The method of claim 25, wherein the subject is suffering from diabetes, hypertension, sleep apnea, cardiovascular disease.

28. The method of claim 25, wherein the subject is suffering from dyslipidemia.

29. The method of claim 25, wherein the amylin analogue is administered subcutaneously.

30. The method of claim 29, wherein administration occurs once weekly.

* * * * *

SEQUENCE LISTING

```
<160> NUMBER OF SEQ ID NOS: 110

<210> SEQ ID NO 1
<211> LENGTH: 37
<212> TYPE: PRT
<213> ORGANISM: Homo sapiens
<220> FEATURE:
<221> NAME/KEY: DISULFID
<222> LOCATION: (2)..(7)
<223> OTHER INFORMATION: A disulphide bridge is formed between residues
      at positions 2 and 7

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Homo sapiens
<220> FEATURE:
<221> NAME/KEY: DISULFID
<222> LOCATION: (2)..(7)
<223> OTHER INFORMATION: A disulphide bridge is formed between residues
      at positions 2 and 7

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: Amino acid sequence Z of Formula I in synthetic
``` amylin analogue which is a compound having the formula R1-Z-R2
<220> FEATURE:
<221> NAME/KEY: VARIANT
<222> LOCATION: (1)..(1)
<223> OTHER INFORMATION: Xaa is selected from the group consisting of
Arg, Lys and Glu
<220> FEATURE:
<221> NAME/KEY: STRAND
<222> LOCATION: (2)..(7)
<223> OTHER INFORMATION: Xaa at positions 2 and 7 are amino acid
residues whose side chains together form a lactam bridge
<220> FEATURE:
<221> NAME/KEY: VARIANT
<222> LOCATION: (2)..(2)
<223> OTHER INFORMATION: Xaa2 can be Asp, Glu, Aad, Dap, Dab, Orn, Lys,
or hLys. If Xaa2 is Asp, Glu, or Aad, then Xaa7 is Dap, Dab, Orn,
Lys, or hLys. If Xaa2 is Dap, Dab, Orn, Lys, or hLys, then Xaa7 is
Asp, Glu, or Aad. See the feature 'VARIANT' of position 7 for more
information
<220> FEATURE:
<221> NAME/KEY: VARIANT
<222> LOCATION: (3)..(3)
<223> OTHER INFORMATION: Xaa is selected from the group consisting of
Gly, Gln and Pro
<220> FEATURE:
<221> NAME/KEY: VARIANT
<222> LOCATION: (4)..(4)
<223> OTHER INFORMATION: Xaa is selected from the group consisting of
Thr and Glu
<220> FEATURE:
<221> NAME/KEY: VARIANT
<222> LOCATION: (5)..(5)
<223> OTHER INFORMATION: Xaa is selected from the group consisting of
Ala and Leu
<220> FEATURE:
<221> NAME/KEY: VARIANT
<222> LOCATION: (6)..(6)
<223> OTHER INFORMATION: Xaa is selected from the group consisting of
Thr and Ser
<220> FEATURE:
<221> NAME/KEY: VARIANT
<222> LOCATION: (7)..(7)
<223> OTHER INFORMATION: Information about Xaa7 is detailed in the
feature labeled as 'VARIANT' for position 2 of this sequence.
Dap = Diaminopropionic acid, Dab = 2,4-Diaminobutanoic acid, and
hLys = 2-amino-7-amino-heptanoic acid, also known as homo-lysine
<220> FEATURE:
<221> NAME/KEY: VARIANT
<222> LOCATION: (10)..(10)
<223> OTHER INFORMATION: Xaa is selected from the group consisting of
Glu and Gln
<220> FEATURE:
<221> NAME/KEY: VARIANT
<222> LOCATION: (14)..(14)
<223> OTHER INFORMATION: Xaa is selected from the group consisting of
Aad, His, Asp, Asn and Arg
<220> FEATURE:
<221> NAME/KEY: VARIANT
<222> LOCATION: (17)..(17)
<223> OTHER INFORMATION: Xaa is selected from the group consisting of
Gln, His and Thr
<220> FEATURE:
<221> NAME/KEY: VARIANT
<222> LOCATION: (19)..(20)
<223> OTHER INFORMATION: Xaa-Xaa is selected from Ser-Ser, Thr-Thr,
Ala-Thr, Ala-Ala, Gly-Thr, Gly-Gly and Ala-Asn or is absent
<220> FEATURE:
<221> NAME/KEY: SITE
<222> LOCATION: (21)..(22)
<223> OTHER INFORMATION: Xaa21-Xaa22 are absent
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:

```
<221> NAME/KEY: VARIANT
<222> LOCATION: (27)..(27)
<223> OTHER INFORMATION: Xaa is selected from the group consisting of
      Leu and Pro
<220> FEATURE:
<221> NAME/KEY: VARIANT
<222> LOCATION: (32)..(32)
<223> OTHER INFORMATION: Xaa is selected from the group consisting of
      Val and Thr
<220> FEATURE:
<221> NAME/KEY: VARIANT
<222> LOCATION: (35)..(35)
<223> OTHER INFORMATION: Xaa is selected from the group consisting of
      Asn and Ser
<220> FEATURE:
<221> NAME/KEY: VARIANT
<222> LOCATION: (37)..(37)
<223> OTHER INFORMATION: Xaa is selected from the group consisting of
      4Hyp and Pro

<400> SEQUENCE: 3

Xaa Xaa Xaa Xaa Xaa Xaa Xaa Ala Thr Xaa Arg Leu Ala Xaa Phe Leu
1               5                   10                  15

Xaa Arg Xaa Xaa Xaa Xaa Phe Xaa Ala Xaa Xaa Ser Ser Thr Glu Xaa
            20                  25                  30

Gly Ser Xaa Thr Xaa
        35

<210> SEQ ID NO 4
<211> LENGTH: 37
<212> TYPE: PRT
<213> ORGANISM: Artificial Sequence
<220> FEATURE:
<223> OTHER INFORMATION: Amino acid sequence Z of Formula II in
      synthetic amylin analogue which is a compound having the formula
      R1-Z-R2
<220> FEATURE:
<221> NAME/KEY: VARIANT
<222> LOCATION: (1)..(1)
<223> OTHER INFORMATION: Xaa is selected from the group consisting of
      Arg and Lys
<220> FEATURE:
<221> NAME/KEY: STRAND
<222> LOCATION: (2)..(7)
<223> OTHER INFORMATION: Xaa2 and Xaa7 are amino acid residues whose
      side chains together form a lactam bridge
<220> FEATURE:
<221> NAME/KEY: VARIANT
<222> LOCATION: (2)..(2)
<223> OTHER INFORMATION: Xaa2 can be Asp, Glu, Aad, Dap, Dab, Orn, Lys,
      or hLys. If Xaa2 is Asp, Glu, or Aad, then Xaa7 is Dap, Dab, Orn,
      Lys, or hLys. If Xaa2 is Dap, Dab, Orn, Lys, or hLys, then Xaa7 is
      Asp, Glu, or Aad. See the feature 'VARIANT' of position 7 for more
      information
<220> FEATURE:
<221> NAME/KEY: VARIANT
<222> LOCATION: (7)..(7)
<223> OTHER INFORMATION: Information about Xaa7 is detailed in the
      feature labeled as 'VARIANT' for position 2 of this sequence.
      Dap = Diaminopropionic acid, Dab = 2,4-Diaminobutanoic acid, and
      hLys = 2-amino-7-amino-heptanoic acid, also known as homo-lysine
<220> FEATURE:
<221> NAME/KEY: VARIANT
<222> LOCATION: (10)..(10)
<223> OTHER INFORMATION: Xaa is selected from the group consisting of
      Glu and Gln
<220> FEATURE:
<221> NAME/KEY: VARIANT
<222> LOCATION: (14)..(14)
<223> OTHER INFORMATION: Xaa is selected from the group consisting of
      Aad, Asp and His
<220> FEATURE:
<221> NAME/KEY: VARIANT
<222> LOCATION: (19)..(20)
<223> OTHER INFORMATION: Xaa19 and Xaa20 is selected from Ser-Ser and
```

```
                Thr-Thr or is absent
<220> FEATURE:
<221> NAME/KEY: SITE
<222> LOCATION: (21)..(22)
<223> OTHER INFORMATION: Xaa21 and Xaa22 are absent
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: VARIANT
<222> LOCATION: (27)..(27)
<223> OTHER INFORMATION: Xaa is selected from the group consisting of
      Leu and Pro
<220> FEATURE:
<221> NAME/KEY: MOD_RES
<222> LOCATION: (37)..(37)
<223> OTHER INFORMATION: 4Hyp

<400> SEQUENCE: 4

Xaa Xaa Gly Thr Ala Thr Xaa Ala Thr Xaa Arg Leu Ala Xaa Phe Leu
1               5                   10                  15

Gln Arg Xaa Xaa Xaa Xaa Phe Xaa Ala Xaa Xaa Ser Ser Thr Glu Val
            20                  25                  30

Gly Ser Asn Thr Xaa
            35

<210> SEQ ID NO 5
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Diaminopropionic acid (Dap)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 5

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 6
<211> LENGTH: 35
<212> TYPE: PRT
```

```
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 6

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 7
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 7

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35
```

```
<210> SEQ ID NO 8
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 8

Arg Asp Gly Thr Ala Thr Xaa Ala Thr Glu Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 9
<211> LENGTH: 33
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle
<220> FEATURE:
<221> NAME/KEY: MOD_RES
<222> LOCATION: (33)..(33)
<223> OTHER INFORMATION: 4Hyp

<400> SEQUENCE: 9

Arg Asp Gly Thr Ala Thr Xaa Ala Thr Glu Arg Leu Ala His Phe Leu
1               5                   10                  15

Gln Arg Phe Xaa Ala Xaa Leu Ser Ser Thr Glu Val Gly Ser Asn Thr
            20                  25                  30

Xaa
```

```
<210> SEQ ID NO 10
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 10

Arg Asp Gly Thr Ala Thr Xaa Ala Thr Glu Arg Leu Ala His Phe Leu
1               5                   10                  15

His Arg Ser Ser Phe Xaa Ala Xaa Leu Ser Ser Thr Glu Val Gly Ser
            20                  25                  30

Asn Thr Pro
        35

<210> SEQ ID NO 11
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 11

Arg Asp Gly Thr Ala Thr Xaa Ala Thr Gln Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35
```

```
<210> SEQ ID NO 12
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 12

Arg Asp Gly Thr Ala Thr Xaa Ala Thr Gln Arg Leu Ala His Phe Leu
1               5                  10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 13
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 13

Arg Asp Gly Thr Ala Thr Xaa Ala Thr Glu Arg Leu Ala Arg Phe Leu
1               5                  10                  15

Gln Arg Ser Ser Phe Xaa Ala Xaa Leu Ser Ser Thr Glu Val Gly Ser
            20                  25                  30
```

Asn Thr Xaa
        35

<210> SEQ ID NO 14
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 14

Glu Asp Gly Thr Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 15
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 15

Arg Asp Gly Glu Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 16

```
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 16

Arg Asp Gly Thr Leu Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 17
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 17

Arg Asp Gly Thr Ala Ser Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 18
<211> LENGTH: 35
<212> TYPE: PRT
<213> ORGANISM: Artificial Sequence
<220> FEATURE:
<223> OTHER INFORMATION: Amino acid sequence Z in synthetic amylin
```

```
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 18

Arg Asp Gly Thr Ala Thr Lys Ala Thr Gln Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 19
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 19

Arg Asp Gly Thr Ala Thr Lys Ala Thr Gln Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 20
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
```

```
              positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 20

Arg Asp Gly Thr Ala Thr Lys Ala Thr Glu Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 21
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 21

Arg Asp Gly Thr Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 22
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is 2-amino-7-amino-heptanoic acid, also
```

```
            known as homo-lysine
<220> FEATURE:
<221> NAME/KEY: MISC_FEATURE
<222> LOCATION: (7)..(7)
<223> OTHER INFORMATION: Xaa is 2-amino-7-amino-heptanoic acid, also
      known as homo-lysine
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 22

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 23
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 23

Arg Asp Gly Thr Ala Thr Xaa Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 24
<211> LENGTH: 35
<212> TYPE: PRT
```

-continued

```
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 24

Arg Asp Gly Thr Ala Thr Xaa Ala Thr Glu Arg Leu Ala Xaa Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 25
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 25

Arg Asp Gly Thr Ala Thr Xaa Ala Thr Glu Arg Leu Ala Xaa Phe Leu
1               5                   10                  15
```

```
Thr Arg Ser Ser Phe Xaa Ala Xaa Leu Ser Ser Thr Glu Val Gly Ser
            20                  25                  30

Ser Thr Xaa
        35

<210> SEQ ID NO 26
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 26

Arg Asp Gly Thr Ala Thr Xaa Ala Thr Glu Arg Leu Ala Xaa Phe Leu
1               5                   10                  15

Gln Arg Thr Thr Phe Xaa Ala Xaa Leu Ser Ser Thr Glu Val Gly Ser
            20                  25                  30

Asn Thr Xaa
        35

<210> SEQ ID NO 27
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
```

```
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 27

Arg Asp Gly Thr Ala Thr Xaa Ala Thr Glu Arg Leu Ala Xaa Phe Leu
1               5                   10                  15

Gln Arg Thr Thr Phe Xaa Ala Xaa Pro Ser Ser Thr Glu Val Gly Ser
            20                  25                  30

Asn Thr Xaa
        35

<210> SEQ ID NO 28
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 28

Arg Asp Gly Thr Ala Thr Xaa Ala Thr Glu Arg Leu Ala Xaa Phe Leu
1               5                   10                  15

Gln Arg Ala Thr Phe Xaa Ala Xaa Leu Ser Ser Thr Glu Val Gly Ser
            20                  25                  30

Asn Thr Xaa
        35

<210> SEQ ID NO 29
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
```

```
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 29

Arg Asp Gly Thr Ala Thr Xaa Ala Thr Glu Arg Leu Ala Xaa Phe Leu
1               5                   10                  15

Gln Arg Ala Ala Phe Xaa Ala Xaa Leu Ser Ser Thr Glu Val Gly Ser
            20                  25                  30

Asn Thr Xaa
        35

<210> SEQ ID NO 30
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 30

Arg Asp Gly Thr Ala Thr Xaa Ala Thr Glu Arg Leu Ala Xaa Phe Leu
1               5                   10                  15

Gln Arg Gly Thr Phe Xaa Ala Xaa Leu Ser Ser Thr Glu Val Gly Ser
            20                  25                  30

Asn Thr Xaa
        35

<210> SEQ ID NO 31
<211> LENGTH: 35
<212> TYPE: PRT
<213> ORGANISM: Artificial Sequence
```

```
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 31

Arg Asp Gln Thr Ala Thr Xaa Ala Thr Glu Arg Leu Ala Xaa Phe Leu
1               5                   10                  15

Gln Arg Gly Thr Phe Xaa Ala Xaa Leu Ser Ser Thr Glu Val Gly Ser
            20                  25                  30

Asn Thr Xaa
        35

<210> SEQ ID NO 32
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 32

Arg Asp Pro Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
```

```
<210> SEQ ID NO 33
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 33

Glu Asp Gly Thr Ala Thr Lys Ala Thr Glu Arg Leu Ala Xaa Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 34
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 34

Arg Asp Gly Thr Ala Thr Lys Ala Thr Glu Arg Leu Ala Xaa Phe Leu
1               5                   10                  15

Gln Arg Ala Ala Phe Xaa Ala Xaa Leu Ser Ser Thr Glu Val Gly Ser
            20                  25                  30
```

Asn Thr Xaa
        35

<210> SEQ ID NO 35
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 35

Arg Asp Gly Thr Ala Thr Lys Ala Thr Glu Arg Leu Ala Xaa Phe Leu
1               5                   10                  15

Gln Arg Gly Gly Phe Xaa Ala Xaa Leu Ser Ser Thr Glu Val Gly Ser
            20                  25                  30

Asn Thr Xaa
        35

<210> SEQ ID NO 36
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 36

Arg Asp Gly Thr Ala Thr Lys Ala Thr Glu Arg Leu Ala Xaa Phe Leu

```
                1               5                  10                  15
Gln Arg Ala Asn Phe Xaa Ala Xaa Leu Ser Ser Thr Glu Val Gly Ser
                    20                  25                  30

Asn Thr Xaa
        35

<210> SEQ ID NO 37
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 37

Arg Asp Gly Thr Ala Thr Lys Ala Thr Glu Arg Leu Ala Xaa Phe Leu
1               5                  10                  15

Gln Arg Ser Ser Phe Xaa Ala Xaa Pro Ser Ser Thr Glu Val Gly Ser
                    20                  25                  30

Asn Thr Xaa
        35

<210> SEQ ID NO 38
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp
```

```
<400> SEQUENCE: 38

Arg Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 39
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 39

Arg Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Thr Gly Ser
            20                  25                  30

Asn Thr Xaa
        35

<210> SEQ ID NO 40
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
```

<222> LOCATION: (35)..(35)
<223> OTHER INFORMATION: 4Hyp

<400> SEQUENCE: 40

Glu Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 41
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 41

Arg Asp Gly Thr Ala Thr Lys Ala Thr Glu Arg Leu Ala Xaa Phe Leu
1               5                   10                  15

Gln Arg Thr Thr Phe Xaa Ala Xaa Leu Ser Ser Thr Glu Val Gly Ser
            20                  25                  30

Asn Thr Xaa
        35

<210> SEQ ID NO 42
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)

```
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 42

Lys Asp Gly Thr Ala Thr Lys Ala Thr Gln Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 43
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 43

Arg Asp Gly Thr Ala Thr Lys Ala Thr Gln Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 44
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
```

```
<220> FEATURE:
<221> NAME/KEY: MOD_RES
<222> LOCATION: (35)..(35)
<223> OTHER INFORMATION: 4Hyp

<400> SEQUENCE: 44

Arg Asp Gly Thr Ala Thr Lys Ala Thr Gln Arg Leu Ala Asp Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 45
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 45

Arg Asp Gly Thr Ala Thr Lys Ala Thr Gln Arg Leu Ala Asp Phe Leu
1               5                   10                  15

Gln Arg Ser Ser Phe Xaa Ala Xaa Leu Ser Ser Thr Glu Thr Gly Ser
            20                  25                  30

Asn Thr Xaa
        35

<210> SEQ ID NO 46
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp
```

```
<400> SEQUENCE: 46

Lys Asp Gly Thr Ala Thr Lys Ala Thr Gln Arg Leu Ala Asn Phe Leu
1               5                   10                  15

Gln Arg Ser Ser Phe Xaa Ala Xaa Leu Ser Ser Thr Glu Val Gly Ser
                20                  25                  30

Asn Thr Xaa
        35

<210> SEQ ID NO 47
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 47

Lys Asp Gly Thr Ala Thr Lys Ala Thr Gln Arg Leu Ala Asn Phe Leu
1               5                   10                  15

Gln Arg Ser Ser Phe Xaa Ala Xaa Leu Ser Ser Thr Glu Thr Gly Ser
                20                  25                  30

Asn Thr Xaa
        35

<210> SEQ ID NO 48
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is Diaminopropionic acid (Dap)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 48
```

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 49
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 49

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 50
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)

<223> OTHER INFORMATION: 4Hyp

<400> SEQUENCE: 50

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 51
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is Diaminopropionic acid (Dap)
<220> FEATURE:
<221> NAME/KEY: MISC_FEATURE
<222> LOCATION: (7)..(7)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 51

Arg Xaa Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 52
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly

```
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 52

Arg Xaa Gly Thr Ala Thr Glu Ala Thr Glu Arg Leu Ala His Phe Leu
 1               5                  10                  15

Gln Arg Ser Ser Phe Xaa Ala Xaa Leu Ser Ser Thr Glu Val Gly Ser
             20                  25                  30

Asn Thr Xaa
         35

<210> SEQ ID NO 53
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
<221> NAME/KEY: MISC_FEATURE
<222> LOCATION: (2)..(2)
<223> OTHER INFORMATION: Xaa is Aad
<220> FEATURE:
<221> NAME/KEY: MISC_FEATURE
<222> LOCATION: (7)..(7)
<223> OTHER INFORMATION: Xaa is Diaminopropionic acid (Dap)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 53

Arg Xaa Gly Thr Ala Thr Xaa Ala Thr Glu Arg Leu Ala His Phe Leu
 1               5                  10                  15

Gln Arg Ser Ser Phe Xaa Ala Xaa Leu Ser Ser Thr Glu Val Gly Ser
             20                  25                  30

Asn Thr Xaa
         35

<210> SEQ ID NO 54
<211> LENGTH: 35
<212> TYPE: PRT
<213> ORGANISM: Artificial Sequence
<220> FEATURE:
<223> OTHER INFORMATION: Amino acid sequence Z in synthetic amylin
      analogue which is a compound having the formula R1-Z-R2
<220> FEATURE:
<221> NAME/KEY: STRAND
<222> LOCATION: (2)..(7)
<223> OTHER INFORMATION: A lactam bridge is formed between residues at
      positions 2 and 7
<220> FEATURE:
```

```
<221> NAME/KEY: MISC_FEATURE
<222> LOCATION: (7)..(7)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 54

Arg Glu Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 55
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Diaminopropionic acid (Dap)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 55

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 56
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
```

```
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 56

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
                20                  25                  30

Asn Thr Xaa
        35

<210> SEQ ID NO 57
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 57

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
                20                  25                  30

Asn Thr Xaa
        35
```

```
<210> SEQ ID NO 58
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 58

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 59
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 59
```

Arg Asp Gly Thr Ala Thr Xaa Ala Thr Glu Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 60
<211> LENGTH: 33
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle
<220> FEATURE:
<221> NAME/KEY: MOD_RES
<222> LOCATION: (33)..(33)
<223> OTHER INFORMATION: 4Hyp

<400> SEQUENCE: 60

Arg Asp Gly Thr Ala Thr Xaa Ala Thr Glu Arg Leu Ala His Phe Leu
1               5                   10                  15

Gln Arg Phe Xaa Ala Xaa Leu Ser Ser Thr Glu Val Gly Ser Asn Thr
            20                  25                  30

Xaa

<210> SEQ ID NO 61
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 3 and 8
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:

```
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 61

Arg Asp Gly Thr Ala Thr Xaa Ala Thr Glu Arg Leu Ala His Phe Leu
1               5                   10                  15

His Arg Ser Ser Phe Xaa Ala Xaa Leu Ser Ser Thr Glu Val Gly Ser
            20                  25                  30

Asn Thr Pro
        35

<210> SEQ ID NO 62
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 62

Arg Asp Gly Thr Ala Thr Xaa Ala Thr Gln Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 63
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
```

```
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 63

Arg Asp Gly Thr Ala Thr Xaa Ala Thr Gln Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 64
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 64

Arg Asp Gly Thr Ala Thr Xaa Ala Thr Glu Arg Leu Ala Arg Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 65
<211> LENGTH: 35
<212> TYPE: PRT
<213> ORGANISM: Artificial Sequence
<220> FEATURE:
<223> OTHER INFORMATION: Synthetic amylin analogue
```

```
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 65

Glu Asp Gly Thr Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 66
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 66

Arg Asp Gly Glu Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 67
<211> LENGTH: 35
<212> TYPE: PRT
<213> ORGANISM: Artificial Sequence
<220> FEATURE:
```

```
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 67

Arg Asp Gly Thr Leu Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 68
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 68

Arg Asp Gly Thr Ala Ser Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 69
<211> LENGTH: 35
<212> TYPE: PRT
<213> ORGANISM: Artificial Sequence
```

```
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 69

Arg Asp Gly Thr Ala Thr Lys Ala Thr Gln Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 70
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 70

Arg Asp Gly Thr Ala Thr Lys Ala Thr Gln Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 71
<211> LENGTH: 35
<212> TYPE: PRT
```

```
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 71

Arg Asp Gly Thr Ala Thr Lys Ala Thr Glu Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 72
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 72

Arg Asp Gly Thr Ala Thr Lys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 73
<211> LENGTH: 35
```

```
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is 2-amino-7-amino-heptanoic acid, also
      known as homo-lysine
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 73

Arg Asp Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 74
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp
```

<400> SEQUENCE: 74

Arg Asp Gly Thr Ala Thr Xaa Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 75
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 75

Arg Asp Gly Thr Ala Thr Xaa Ala Thr Glu Arg Leu Ala Xaa Phe Leu
1               5                   10                  15

Gln Arg Ser Ser Phe Xaa Ala Xaa Pro Ser Thr Glu Val Gly Ser
            20                  25                  30

Asn Thr Xaa
        35

<210> SEQ ID NO 76
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn

```
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 76

Arg Asp Gly Thr Ala Thr Xaa Ala Thr Glu Arg Leu Ala Xaa Phe Leu
1               5                   10                  15

Thr Arg Ser Ser Phe Xaa Ala Xaa Leu Ser Ser Thr Glu Val Gly Ser
            20                  25                  30

Ser Thr Xaa
        35

<210> SEQ ID NO 77
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 77

Arg Asp Gly Thr Ala Thr Xaa Ala Thr Glu Arg Leu Ala Xaa Phe Leu
1               5                   10                  15

Gln Arg Thr Thr Phe Xaa Ala Xaa Leu Ser Ser Thr Glu Val Gly Ser
            20                  25                  30

Asn Thr Xaa
        35

<210> SEQ ID NO 78
<211> LENGTH: 35
```

```
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 78

Arg Asp Gly Thr Ala Thr Xaa Ala Thr Glu Arg Leu Ala Xaa Phe Leu
1               5                   10                  15

Gln Arg Thr Thr Phe Xaa Ala Xaa Pro Ser Ser Thr Glu Val Gly Ser
            20                  25                  30

Asn Thr Xaa
        35

<210> SEQ ID NO 79
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
```

<222> LOCATION: (35)..(35)
<223> OTHER INFORMATION: 4Hyp

<400> SEQUENCE: 79

Arg Asp Gly Thr Ala Thr Xaa Ala Thr Glu Arg Leu Ala Xaa Phe Leu
1               5                   10                  15

Gln Arg Ala Thr Phe Xaa Ala Xaa Leu Ser Ser Thr Glu Val Gly Ser
            20                  25                  30

Asn Thr Xaa
        35

<210> SEQ ID NO 80
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 80

Arg Asp Gly Thr Ala Thr Xaa Ala Thr Glu Arg Leu Ala Xaa Phe Leu
1               5                   10                  15

Gln Arg Ala Ala Phe Xaa Ala Xaa Leu Ser Ser Thr Glu Val Gly Ser
            20                  25                  30

Asn Thr Xaa
        35

<210> SEQ ID NO 81
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:

```
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 81

Arg Asp Gly Thr Ala Thr Xaa Ala Thr Glu Arg Leu Ala Xaa Phe Leu
1               5                   10                  15

Gln Arg Gly Thr Phe Xaa Ala Xaa Leu Ser Ser Thr Glu Val Gly Ser
            20                  25                  30

Asn Thr Xaa
        35

<210> SEQ ID NO 82
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 82

Arg Asp Gln Thr Ala Thr Xaa Ala Thr Glu Arg Leu Ala Xaa Phe Leu
1               5                   10                  15

Gln Arg Gly Thr Phe Xaa Ala Xaa Leu Ser Ser Thr Glu Val Gly Ser
            20                  25                  30

Asn Thr Xaa
        35
```

```
<210> SEQ ID NO 83
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 83

Arg Asp Pro Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 84
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 84
```

```
Glu Asp Gly Thr Ala Thr Lys Ala Thr Glu Arg Leu Ala Xaa Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 85
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 85

Arg Asp Gly Thr Ala Thr Lys Ala Thr Glu Arg Leu Ala Xaa Phe Leu
1               5                   10                  15

Gln Arg Ala Ala Phe Xaa Ala Xaa Leu Ser Ser Thr Glu Val Gly Ser
            20                  25                  30

Asn Thr Xaa
        35

<210> SEQ ID NO 86
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
```

```
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 86

Arg Asp Gly Thr Ala Thr Lys Ala Thr Glu Arg Leu Ala Xaa Phe Leu
1               5                   10                  15

Gln Arg Gly Gly Phe Xaa Ala Xaa Leu Ser Ser Thr Glu Val Gly Ser
            20                  25                  30

Asn Thr Xaa
        35

<210> SEQ ID NO 87
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 87

Arg Asp Gly Thr Ala Thr Lys Ala Thr Glu Arg Leu Ala Xaa Phe Leu
1               5                   10                  15

Gln Arg Ala Asn Phe Xaa Ala Xaa Leu Ser Ser Thr Glu Val Gly Ser
            20                  25                  30

Asn Thr Xaa
        35

<210> SEQ ID NO 88
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
```

```
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 88

Arg Asp Gly Thr Ala Thr Lys Ala Thr Glu Arg Leu Ala Xaa Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 89
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 89

Arg Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 90
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
```

```
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 90

Arg Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Thr Gly Ser
            20                  25                  30

Asn Thr Xaa
        35

<210> SEQ ID NO 91
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 91

Glu Asp Gly Thr Ala Thr Lys Ala Thr Glu Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35
```

```
<210> SEQ ID NO 92
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 92

Arg Asp Gly Thr Ala Thr Lys Ala Thr Glu Arg Leu Ala Xaa Phe Leu
1               5                   10                  15

Gln Arg Thr Thr Phe Xaa Ala Xaa Leu Ser Ser Thr Glu Val Gly Ser
            20                  25                  30

Asn Thr Xaa
        35

<210> SEQ ID NO 93
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 93
```

```
Lys Asp Gly Thr Ala Thr Lys Ala Thr Gln Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 94
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 94

Arg Asp Gly Thr Ala Thr Lys Ala Thr Gln Arg Leu Ala Xaa Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 95
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
```

<221> NAME/KEY: MOD_RES
<222> LOCATION: (35)..(35)
<223> OTHER INFORMATION: 4Hyp

<400> SEQUENCE: 95

Arg Asp Gly Thr Ala Thr Lys Ala Thr Gln Arg Leu Ala Asp Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 96
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 96

Arg Asp Gly Thr Ala Thr Lys Ala Thr Gln Arg Leu Ala Asp Phe Leu
1               5                   10                  15

Gln Arg Ser Ser Phe Xaa Ala Xaa Leu Ser Ser Thr Glu Thr Gly Ser
            20                  25                  30

Asn Thr Xaa
        35

<210> SEQ ID NO 97
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

```
<220> FEATURE:
<221> NAME/KEY: MOD_RES
<222> LOCATION: (35)..(35)
<223> OTHER INFORMATION: 4Hyp

<400> SEQUENCE: 97

Lys Asp Gly Thr Ala Thr Lys Ala Thr Gln Arg Leu Ala Asn Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 98
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 98

Lys Asp Gly Thr Ala Thr Lys Ala Thr Gln Arg Leu Ala Asn Phe Leu
1               5                   10                  15

Gln Arg Ser Ser Phe Xaa Ala Xaa Leu Ser Ser Thr Glu Thr Gly Ser
            20                  25                  30

Asn Thr Xaa
        35

<210> SEQ ID NO 99
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (2)..(2)
<223> OTHER INFORMATION: Xaa is Diaminopropionic acid (Dap)
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
```

```
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 99

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 100
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (2)..(2)
<223> OTHER INFORMATION: Xaa is 2,4-Diaminobutanoic acid (Dab)
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 100

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 101
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (2)..(2)
```

```
<223> OTHER INFORMATION: Xaa is Orn
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 101

Arg Xaa Gly Thr Ala Thr Asp Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 102
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (2)..(2)
<223> OTHER INFORMATION: Xaa is Diaminopropionic acid (Dap)
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 102

Arg Xaa Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35
```

```
<210> SEQ ID NO 103
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (2)..(2)
<223> OTHER INFORMATION: Xaa is 2,4-Diaminobutanoic acid (Dab)
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 103

Arg Xaa Gly Thr Ala Thr Glu Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 104
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (2)..(2)
<223> OTHER INFORMATION: Xaa is Aad
<220> FEATURE:
<221> NAME/KEY: MISC_FEATURE
<222> LOCATION: (7)..(7)
<223> OTHER INFORMATION: Xaa is Diaminopropionic acid (Dap)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp
```

<400> SEQUENCE: 104

Arg Xaa Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 105
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: STRAND
<222> LOCATION: (2)..(7)
<223> OTHER INFORMATION: An amide bond is formed between the side chains
      at positions 2 and 7
<220> FEATURE:
<221> NAME/KEY: MISC_FEATURE
<222> LOCATION: (7)..(7)
<223> OTHER INFORMATION: Xaa is 2,4-Diaminobutanoic acid (Dab)
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 105

Arg Glu Gly Thr Ala Thr Xaa Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 106
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

```
<220> FEATURE:
<221> NAME/KEY: MOD_RES
<222> LOCATION: (35)..(35)
<223> OTHER INFORMATION: 4Hyp

<400> SEQUENCE: 106

Arg Asp Gly Thr Ala Thr Xaa Ala Thr Glu Arg Leu Ala His Phe Leu
1               5                   10                  15

Gln Arg Ser Ser Phe Xaa Ala Xaa Pro Ser Ser Thr Glu Val Gly Ser
            20                  25                  30

Asn Thr Xaa
        35

<210> SEQ ID NO 107
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: DISULFID
<222> LOCATION: (2)..(7)
<223> OTHER INFORMATION: intramolecular disulphide bridge formed between
      the cysteine residues present at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 107

Arg Cys Gly Thr Ala Thr Cys Ala Thr Glu Arg Leu Ala His Phe Leu
1               5                   10                  15

Gln Arg Ser Ser Phe Xaa Ala Xaa Leu Ser Ser Thr Glu Val Gly Ser
            20                  25                  30

Asn Thr Xaa
        35

<210> SEQ ID NO 108
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: MISC_FEATURE
<222> LOCATION: (7)..(7)
<223> OTHER INFORMATION: Xaa is Orn
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
```

```
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 108

Arg Asp Gly Thr Ala Thr Xaa Ala Thr Glu Arg Leu Ala Xaa Phe Leu
 1               5                  10                  15

Gln Arg Ser Ser Phe Xaa Ala Xaa Leu Ser Ser Thr Glu Val Gly Ser
             20                  25                  30

Asn Thr Xaa
         35

<210> SEQ ID NO 109
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: DISULFID
<222> LOCATION: (2)..(7)
<223> OTHER INFORMATION: Intramolecular disulphide bridge formed between
      the cysteine residues persent at positions 2 and 7
<220> FEATURE:
<221> NAME/KEY: MISC_FEATURE
<222> LOCATION: (14)..(14)
<223> OTHER INFORMATION: Xaa is Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 109

Arg Cys Gly Thr Ala Thr Cys Ala Thr Glu Arg Leu Ala Xaa Phe Leu
 1               5                  10                  15

Gln Arg Ser Ser Phe Xaa Ala Xaa Leu Ser Ser Thr Glu Val Gly Ser
             20                  25                  30

Asn Thr Xaa
         35

<210> SEQ ID NO 110
<211> LENGTH: 35
<212> TYPE: PRT
<213> ORGANISM: Artificial Sequence
<220> FEATURE:
<223> OTHER INFORMATION: Synthetic amylin analogue
<220> FEATURE:
<221> NAME/KEY: MOD_RES
<222> LOCATION: (1)..(1)
<223> OTHER INFORMATION: [19-carboxynonadecanoyl]-isoGlu
<220> FEATURE:
<221> NAME/KEY: DISULFID
<222> LOCATION: (2)..(7)
<223> OTHER INFORMATION: Intramolecular disulphide bridge formed between
```

```
                    the cysteine residues present at positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 110

Arg Cys Asn Thr Ala Thr Cys Ala Thr Gln Arg Leu Ala Asp Phe Leu
1               5                   10                  15

Gln Arg Ser Ser Phe Xaa Ala Xaa Leu Ser Ser Thr Glu Val Gly Ser
            20                  25                  30

Asn Thr Xaa
        35
```